(12) United States Patent
Jones et al.

(10) Patent No.: US 9,315,523 B2
(45) Date of Patent: Apr. 19, 2016

(54) CYCLIC DINUCLEOSIDES

(71) Applicant: Rutgers, the State University of New Jersey, New Brunswick, NJ (US)

(72) Inventors: Roger A. Jones, New Brunswick, NJ (US); Barbara L. Gaffney, New Brunswick, NJ (US)

(73) Assignee: Rutgers, The State University of New Jersey, New Brunswick, NJ (US)

( * ) Notice: Subject to any disclaimer, the term of this patent is extended or adjusted under 35 U.S.C. 154(b) by 0 days.

(21) Appl. No.: 14/562,203

(22) Filed: Dec. 5, 2014

(65) Prior Publication Data

US 2015/0158886 A1 Jun. 11, 2015

Related U.S. Application Data

(60) Provisional application No. 61/913,019, filed on Dec. 6, 2013.

(51) Int. Cl.
| | | |
|---|---|---|
| C07H 19/20 | (2006.01) | |
| C07H 21/02 | (2006.01) | |
| C07D 519/00 | (2006.01) | |

(52) U.S. Cl.
CPC .................................. *C07D 519/00* (2013.01)

(58) Field of Classification Search
CPC ............................... C07H 19/20; C07H 21/02
See application file for complete search history.

(56) References Cited

U.S. PATENT DOCUMENTS

| | | | |
|---|---|---|---|
| 4,559,157 | A | 12/1985 | Smith |
| 4,608,392 | A | 8/1986 | Jacquet |
| 4,820,508 | A | 4/1989 | Wortzman |
| 4,938,949 | A | 7/1990 | Borch |
| 4,992,478 | A | 2/1991 | Geria |
| 7,709,458 | B2 | 5/2010 | Karaolis et al. |
| 8,450,293 | B2 | 5/2013 | Jones et al. |
| 2012/0178710 | A1 | 7/2012 | Jones et al. |

FOREIGN PATENT DOCUMENTS

| | | |
|---|---|---|
| WO | 2005030186 A2 | 4/2005 |
| WO | 2006045041 A2 | 4/2006 |
| WO | 2011003025 A1 | 1/2011 |

OTHER PUBLICATIONS

Ali et al., "A greener synthetic protocol for the preparation of carbodiimide", Tetrahedron Lett 51, 1019-1021 (2010).
Amiot et al., "New Approach for the Synthesis of c-di-GMP and Its Analogues", Synthesis, 24, 4230-4236, (2006).
Asadi et al., "G^ C Quartet—A DNA-Inspired Janus-GC Heterocycle: Synthesis, Structural Analysis and Self-Organization", J. Am. Chem. Soc., 130, 12860-12861, (2008).
Burdette et al., "STING is a direct innate immune sensor of cyclic di-Gmp", Nature 478, 515-518 (2011).
Ching et al., "Synthesis of cyclic di-nucleotidic acids as potential inhibitors targeting diguanylate cyclase", Biorg. Med. Chem., 18, 6657-6665, (2010).
Cho et al., "15N Nuclear Magnetic Resonance Studies on the Tautomerism of 8-Hydroxy-2'-deoxyguanosine, 8-Hydroxyguanosine, and Other C8-Substituted Guanine Nucleosides1", Chem. Res. Toxicol., 3, 445-452, (1990).
Dean, "Synthetic Communications: An International Journal for Rapid Communication of Synthetic Organic Chemistry", Synthetic Communications 32 (10), 1517-1521 (2002).
Egli et al., "Atomic-resolution structure of the cellulose synthase regulator cyclic diguanylic acid", Proc. Natl. Acad. Sci., vol. 87, 3235-3239, (1990).
Gaffney et al., "One-Flask Syntheses of c-di-GMP and the [Rp,Rp] and [Rp,Sp] Thiophosphate Analogues", Organic Letters, vol. 12, No. 14, 3269-3271, (2010).
Gaffney et al., "Synthesis of c-di-GMP Analogs with Thiourea, Urea, Carbodiimide, and Guanidinium Linkages", Org Lett 16(1), 158-161 (2014).
Gao et al., "Structure-Function Analysis of Sting Activation by c[G(2',5')pA(3',5')p] and Targeting by Antiviral DMXAA", Cell 154, 1-15 (2013).
Garcia-Arriaga et al., "Isostructural Self-Assembly of 2'-Deoxyguanosine Derivatives in Aqueous and Organic Media", J. Am. Chem. Soc., 130, 10492-10493, (2008).
He et al., "A convenient preparation of protected 3'-deoxyguanosine from guanosine", Tetrahedron Lett 36, 6991-6994 (1995).
Hengge, "Principles of c-di-GMP signalling in bacteria", Nat Rev Microbiol 7, 263-273 (2009).
Hyodo et al., "Synthesis of cyclic bis(3'-5θ)diguanylic acid (c-di-GMP) analogs", Tetrahedron, 62, 3089-3094, (2006).
Karaolis et al., "Bacterial c-di-GMP is an immunostimulatory molecule", J Immunol 178, 2171-2181 (2007).
Katritzky et al., "Recent developments in guanylating agents", ARKIVOC 2005, 49-87 (2005).
Kiburu et al., "A simple solid-phase synthesis of the ubiquitous bacterial signaling molecule, c-di-GMP and analogues", Mol BioSyst 4, 518-520 (2008).

(Continued)

*Primary Examiner* — Bruck Kifle
(74) *Attorney, Agent, or Firm* — Viksnins Harris & Padys PLLP

(57) ABSTRACT

Provided herein are compounds of formula Ia:

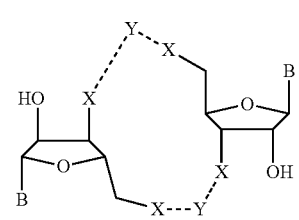

and salts thereof. Also provided are pharmaceutical compositions comprising a compound of formula Ia, processes for preparing compounds of formula Ia, intermediates useful for preparing compounds of formula Ia and therapeutic methods using compounds of formula Ia.

14 Claims, No Drawings

(56) References Cited

OTHER PUBLICATIONS

Kline et al., "Design and Synthesis of bis-Carbamate Analogs of Cyclic bis-(3'-5')-Diguanylic Acid (c-di-GMP) and the Acyclic Dimer PGPG", Nucleosides Nucleotides Nucl. Acids, 27, 1282-1300, (2008).
Ko et al., "Structure of PP4397 reveals the molecular basis for different c-di-GMP binding modes by Pilz domain proteins", J Mol Biol 398, 97-110 (2010).
Krasteva et al., "Sensing the messenger: the diverse ways that bacteria signal through c-di-GMP", Protein Sci 21, 929-948 (2012).
Kroutil et al., "Improved Procedure for the Selective N-Debenzylation of Benzylamines by Diisopropyl Azodicarboxylate", Synthesis (3), 446-450 (2004).
Liaw et al., "Cyclic diguanylic acid behaves as a host molecule for planar intercalators", FEBS J., vol. 264, No. 2, 223-227, (1990).
McGee et al., "Acyclic nucleoside analogues: methods for the preparation of 2',3'-secoguanosine, 5'-deoxy-2',3'- secoguanosine, and(R,S)-9[1-(2-hydroxyethoxy)-2-hydroxyethyl]guanine", Can J Chem 64, 1885-1889 (1986).
Mikolajczyk et al., "Dimethyl Sulphoxide Oxidations: An Iodine-catalysed Conversion of Thio- or Selenophosphoryl and Thiocarbonyl Compounds into Their Oxygen Analogues", Synthesis 2, 114-115 (1975).
Mills et al., "The bacterial second messenger c-di-GMP: mechanisms of signaling", Cell Microbiol 13, 1122-1129 (2011).
Nakayama et al, "Thiazole Orange-Induced c-di-GMP Quadruplex Formation Facilitates a Simple Fluorescent Detection of This Ubiquitous Bioflim Regulating Molecule", J. Am. Chem. Soc., 133, 4856-4864, (2011).
Povolotsky et al., "'Life-style' control networks in *Escherichia coli*: signaling by the second messenger c-di-GMP", J Biotechnol 160, 10-16 (2012).
Quin et al., "The bacterial stressosome: a modular system that has been adapted to control secondary messenger signaling", Structure 20, 350-363 (2012).
Ross et al., "The Cyclic Diguanylic Acid Regulatory System of Cellulose Synthesis in Acetobacter xylinum", J. Biol. Chem., vol. 265, No. 31, 18933-18943, (1990).
Sahu et al., "Oxidation of thiourea and substituted thioureas: a review", Journal of Sulfur Chemistry 32, 171-197 (2011).
Schirmer et al., "Structural and mechanistic determinants of c-di-GMP signaling", Nat Rev Micro 7, 724-735 (2009).
Shanahan et al., "Differential analogue binding by two classes of c-di-GMP riboswitches", J Am Chem Soc 133 (39), 15578-15592 (2011).
Shanahan et al., "Identification of c-di-GMP derivatives resistant to an EAL domain phosphodiesterase", Biochemistry 52, 365-377 (2013).
Smith et al., "Structural basis of ligand binding by a c-di-GMP riboswitch", Nat Struct Mol Biol 16, 1218-1223 (2009).
Smith et al., "Structural and Biochemical Determinants of Ligand Binding by the c-di-GMP Riboswitch", Biochemistry, 49, 7351-7359, (2010).
Smith et al., "Structural basis of differential ligand recognition by two classes of bis-(3'-5')-cyclic dimeric guanosine monophosphate-binding riboswitches", Proc. Natl. Acad. Sci., vol. 108, No. 19, 7757-7762, (2011).
Sondermann et al., "You've come a long way: c-di-GMP signaling", Curr Opin Microbiol 15, 140-146 (2012).
Sudarsan et al., "Riboswitches in eubacteria sense the second messenger cyclic di-GMP", Science 321, 411-413 (2008).
Veliath et al., "Synthesis and characterization of C8 analogs of c-di-GMP", Nucleosides Nucleotides Nucleic Acids, 30(11), 961-978, (2011).
Wang et al., "Conservative Change to the Phosphate Moiety of Cclic Diguanylic Monophosphate Remarkably Affects Its Polymorphism and Ability to Bind DGC, PDE, and PilZ Proteins", J. Am. Chem. Soc., 133, 9320-9330, (2011).
Witte et al., "Structural Biochemistry of a Bacterial Checkpoint Protein Reveals Diadenylate Cyclase Activity Regulated by DNA Recombination Intermediates", Mol. Cell, 30, 167-178, (2008).
Wong et al., "Disodium Guanosine 5'-Monophosphate Self-Associates into Nanoscale Cylinders at pH 8: A Combined Diffusion NMR Spectroscopy and Dynamic Light Scattering Study", J. Am. Chem. Soc., 127, 6990-6998, (2005).
Wong et al., "Isothiocyanates from tosyl chloride mediated decomposition of in situ generated dithiocarbamic acid salts", J Org Chem 72, 3969-3971 (2007).
Woodward et al., "c-di-AMP secreted by intracellular Listeria monocytogenes activates a host type I interferon response", Science 328, 1703-1705 (2010).
Wu e al., "Helical Structure of Disodium 5'-Guanosine Monophosphate Self-Assembly in Neutral Solution", J. Am. Chem. Soc., 131, 3180-3182, (2009).
Yan et al., "Synthesis and Immunostimulatory properties of the phosphorothioate analogues of cdiGMP", Biorg. Med. Chem. Lett., 18, 5631-5634, (2008).
Zhang et al., "c-di-GMP Displays a Monovalent Metal Ion-Dependent Polymorphism", J. Am. Chem. Soc., 126, 16700-16701, (2004).
Zhang et al., "Polymorphism of the Signaling Molecule c-di-GMP", J. Am. Chem. Soc., 128, 7015-7024, (2006).
Zhang et al., "An Efficient Synthesis of 3'-Amino-3'-deoxyguanosine from Guanosine", Hely Chim Acta 86, 703-710 (2003).
Zhao et al., "Thiophosphate Analogs of c-di-GMP: Impact on Polymorphism", Nucleosides Nucleotides Nucl. Acids, 28, 352-378, (2009).
Zhou et al., "Potent suppression of c-di-GMP synthesis via I-site allosteric inhibition of diguanylate cyclases with 2'-F-c-di-GMP", Bioorganic & Medicinal Chemistry 21, 4396-4404 (2013).

CYCLIC DINUCLEOSIDES

CROSS-REFERENCE TO RELATED APPLICATION

This patent application claims the benefit of priority of U.S. application Ser. No. 61/913,019, filed Dec. 6, 2013, which application is herein incorporated by reference.

STATEMENT OF GOVERNMENT SUPPORT

This invention was made with government support under GM79760 awarded by the National Institutes of Health. The government has certain rights in the invention.

BACKGROUND

The bacterial signaling molecule cyclic diguanosine monophosphate (c-di-GMP) is responsible for regulating bacterial responses to a variety of environmental factors, including aggregation into the biofilm state (Hengge, R., Nat. Rev. Microbiol. 2009, 7, 263-273; Krasteva, P. V., et al., Protein Sci. 2012, 21, 929-948; Mills, E.; et al., Cell. Microbiol. 2011, 13, 1122-1129; Povolotsky, T. L.; et al., J. Biotechnol. 2012, 160, 10-16; Quin, M. B.; et al., J., Structure 2012, 20, 350-363; Sondermann, H.; et al., Curr. Opin. Microbiol. 2012, 15, 140-146). Binding of c-di-GMP as a monomer and as a self-intercalated dimer to the PilZ domain proteins has been demonstrated (Hengge, R., Nat. Rev. Microbiol. 2009, 7, 263-273; Krasteva, P. V., et al., Protein Sci. 2012, 21, 929-948; Schirmer, T.; et al., Nat Rev Micro 2009, 7, 724-735; Ko, J.; et al., J. Mol. Biol. 2010, 398, 97-110). Activation of two different classes of riboswitches in noncoding regulatory mRNA domains has also been identified upon binding c-di-GMP (Shanahan, C. A.; et al., J. Am. Chem. Soc. 2011, 134, 15578-15592; Smith, K. D.; et al., Nat. Struct. Mol. Biol. 2009, 16, 1218-1223; Smith, K. D.; Shanahan, C. A.; et al., Proc. Natl. Acad. Sci. USA 2011, 108, 7757-7762; Sudarsan, N.; et al., Science (Wash.) 2008, 321, 411-413). Finally, c-di-GMP, among other cyclic dinucleotides, plays a role in triggering an innate immune response (Karaolis, D. K. R.; et al., J. Immunol. 2007, 178, 2171-2181; Woodward, J. J.; et al., Science 2010, 328, 1703-1705) through a transmembrane protein named STING in the innate immune sensing pathway, where a specific receptor for cyclic dinucleotides has been identified (Burdette, D. L.; et al., Nature 2011, 478, 515-518).

Currently there is a need for agents that are useful for activating the innate immune system. Such activation may be beneficial for treating certain diseases or conditions. There is also a need for agents that are useful for treating bacterial infections, viral infections and/or cancer.

SUMMARY OF THE INVENTION

One embodiment provides a compound of formula I (and formula Ia as described herein):

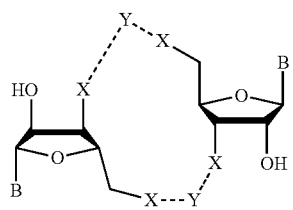

I wherein:
the dashed bonds are single bonds, each X is $NR^a$, and each Y is independently $C(=O)$, $C(=S)$ or $C(=NR^b)$; or the dashed bonds are double bonds, each X is N, and each Y is C;
each $R^a$ is independently H or $(C_1-C_6)$alkyl;
each $R^b$ is independently H or $(C_1-C_6)$alkyl; and
each B is independently

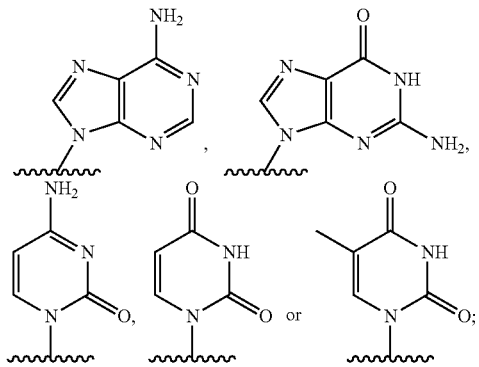

or a salt thereof.

One embodiment provides a pharmaceutical composition comprising a compound of formula I as described herein, or a pharmaceutically acceptable salt thereof and a pharmaceutically acceptable carrier.

One embodiment provides a method of treating a disease or condition (e.g., a bacterial infection) in an mammal (e.g., a human) wherein the activation of the innate immune system would be beneficial for treating the disease or condition comprising administering an effective amount of a compound of formula I as described herein or a pharmaceutically acceptable salt thereof to the mammal.

One embodiment provides a method to activate the innate immune system in a mammal (e.g., a human) in need thereof, comprising administering an effective amount of a compound of formula I as described herein or a pharmaceutically acceptable salt thereof to the mammal.

One embodiment provides a method to treat a bacterial infection in a mammal (e.g., a human) in need thereof, comprising administering an effective amount of a compound of formula I as described herein or a pharmaceutically acceptable salt thereof to the mammal.

One embodiment provides a compound of formula I as described herein or a pharmaceutically acceptable salt thereof for use in medical therapy.

One embodiment provides a compound of formula I as described herein or a pharmaceutically acceptable salt thereof for the prophylactic or therapeutic treatment of a disease or condition (e.g. a bacterial infection) wherein an activated innate immune system would be beneficial for treating the disease or condition.

One embodiment provides a compound of formula I as described herein or a pharmaceutically acceptable salt thereof for the prophylactic or therapeutic activation of the innate immune system.

One embodiment provides a compound of formula I as described herein or a pharmaceutically acceptable salt thereof for the prophylactic or therapeutic treatment of a bacterial infection.

One embodiment provides the use of a compound of formula I as described herein or a pharmaceutically acceptable salt thereof to prepare a medicament for the treatment of a disease or condition (e.g., a bacterial infection) in a mammal (e.g., a human) wherein an activated innate immune system would be beneficial for treating the disease or condition.

One embodiment provides the use of a compound of formula I as described herein or a pharmaceutically acceptable salt thereof to prepare a medicament for the activation of the innate immune system in a mammal (e.g., a human).

One embodiment provides the use of a compound of formula I as described herein or a pharmaceutically acceptable salt thereof to prepare a medicament for the treatment of a bacterial infection in a mammal (e.g., a human).

The invention also provides processes and intermediates disclosed herein that are useful for preparing a compound of formula I or a salt thereof.

DETAILED DESCRIPTION

Compounds described herein may be useful for activating the innate immune system. Activation as used herein means that the innate immune system is in a more active state upon being exposed to a compound described herein when compared to not being exposed to the compound. The activity of the innate immune system may be measured by methods known in the literature. The activation of the immune system may be beneficial for treating a variety of diseases or conditions (Gau, P. et al., Cell, 2013, 154, 1-15, incorporated herein by reference). Accordingly, compounds described herein may be useful for treating cancer, viral infections and bacterial infections. Compounds described herein may also be useful as vaccine adjuvants.

The following definitions are used, unless otherwise described: The term "alkyl" is a straight or branched saturated hydrocarbon. For example, an alkyl group can have 1 to 6 carbon atoms (i.e., $(C_1-C_6$ alkyl) or any number of specified carbon atoms.

It will be appreciated by those skilled in the art that compounds of the invention having a chiral center may exist in and be isolated in optically active and racemic forms. Some compounds may exhibit polymorphism. It is to be understood that the present invention encompasses any racemic, optically-active, polymorphic, or stereoisomeric form, or mixtures thereof, of a compound of the invention, which possess the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase.

When a bond in a compound formula herein is drawn in a non-stereochemical manner (e.g. flat), the atom to which the bond is attached includes all stereochemical possibilities. When a bond in a compound formula herein is drawn in a defined stereochemical manner (e.g. bold, bold-wedge, dashed or dashed-wedge), it is to be understood that the atom to which the stereochemical bond is attached is enriched in the absolute stereoisomer depicted unless otherwise noted. In one embodiment, the compound may be at least 51% the absolute stereoisomer depicted. In another embodiment, the compound may be at least 60% the absolute stereoisomer depicted. In another embodiment, the compound may be at least 80% the absolute stereoisomer depicted. In another embodiment, the compound may be at least 90% the absolute stereoisomer depicted. In another embodiment, the compound may be at least 95 the absolute stereoisomer depicted. In another embodiment, the compound may be at least 99% the absolute stereoisomer depicted.

Specific values listed below for radicals, substituents, and ranges, are for illustration only; they do not exclude other defined values or other values within defined ranges for the radicals and substituents. The specific values are for compounds of formula Ia and all sub-formulas of formula Ia (e.g., formula I). It is to be understood the 2 or more values may be combined.

Specifically, $(C_1-C_6)$alkyl can be methyl, ethyl, propyl, isopropyl, butyl, iso-butyl, sec-butyl, pentyl, 3-pentyl, or hexyl.

A specific group of compounds of formula I are compounds wherein the dashed bonds are single bonds, each X is $NR^a$, and each Y is independently $C(=O)$, $C(=S)$ or $C(=NR^b)$.

A specific value for each $R^a$ is H.

A specific value for each Y is $C(=O)$.

A specific value for each Y is $C(=S)$.

A specific value for each Y is $C(=NR^b)$.

A specific value for each $R^b$ is independently H or methyl.

A specific value for each $R^b$ is H.

A specific value for each $R^b$ is methyl.

A specific group of compounds of formula I are compounds wherein the dashed bonds are double bonds, each X is N, and each Y is C.

A specific value for each B is:

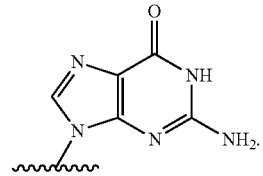 [SMILES: *n1cnc2c(=O)[nH]c(N)nc21]

A compound of formula I selected from

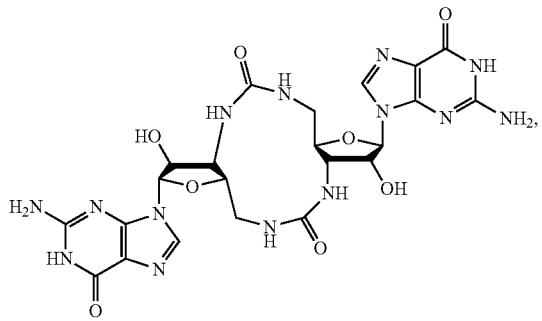

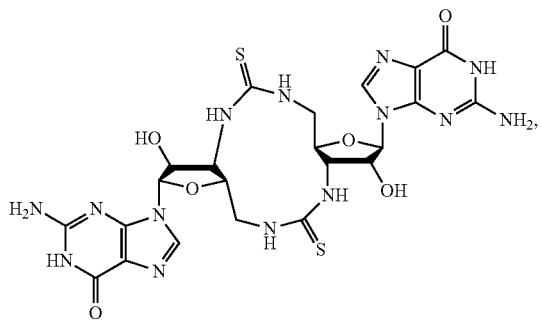

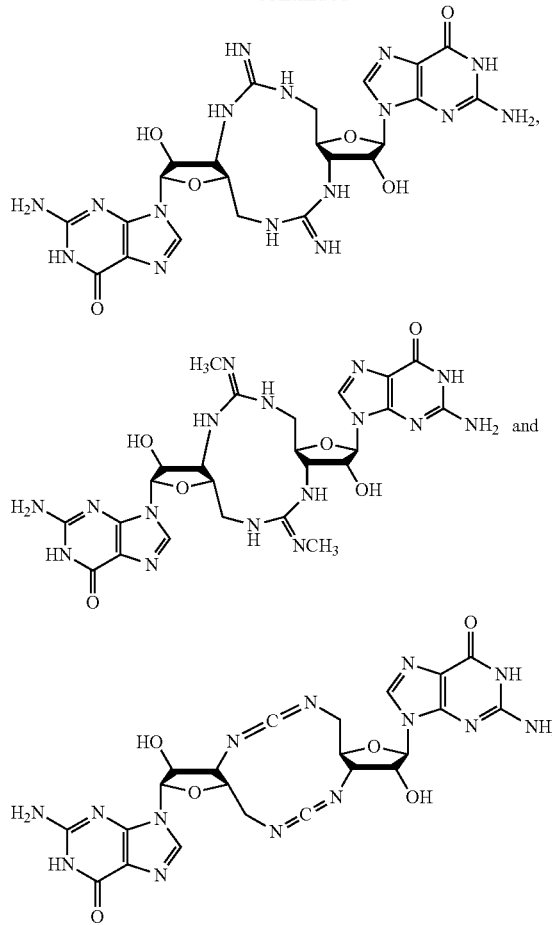

and salts thereof.

One embodiment provides a compound of formula Ia:

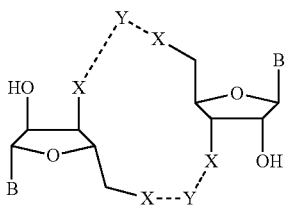

wherein:

the dashed bonds are single bonds, each X is NR$^a$, and each Y is independently C(=O), C(=S) or C(=NR$^b$); or the dashed bonds are double bonds, each X is N, and each Y is C;

each R$^a$ is independently H or (C$_1$-C$_6$)alkyl;
each R$^b$ is independently H or (C$_1$-C$_6$)alkyl; and
each B is independently

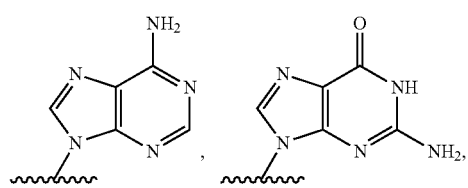

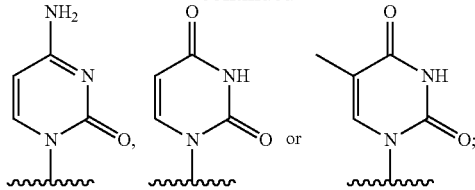

or a salt thereof.

In cases where compounds are sufficiently basic or acidic, a salt of a compound of formula I can be useful as an intermediate for isolating or purifying a compound of formula I. Additionally, administration of a compound of formula I as a pharmaceutically acceptable acid or base salt may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

The compounds of formula I can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound of the invention formulated in such a unit dosage form.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The methods described herein can be useful for treating or preventing a disease or condition that benefits from an activated innate immune system or for treating or preventing a bacterial infection. The term "treatment" or "treating," to the extent it relates to a disorder, disease or condition includes inhibiting the disorder, disease or condition and/or eliminating the disorder, disease or condition and/or relieving one or more symptoms of the disorder, disease or condition. The term "preventing" or "prevention" includes preventing the disorder, disease or condition from occurring or lessening the severity of the disorder, disease or condition.

The invention will now be illustrated by the following non-limiting Examples

Example 1

Synthetic Routes and Schemes

It is to be understood the synthetic schemes provided can be used to prepare additional compounds of formula I. One embodiment provides any of the synthetic routes, intermediates or compounds described herein below. A number of synthetic routes to c-di-GMP and its thiophosphate analogs have been reported (Gaffney, B. L.; et al., Org. Lett. 2010, 12, 3269-3271; Kiburu, I.; et al., Mol. BioSyst. 2008, 4, 518-520; Yan, H.; et al., Biorg. Med. Chem. Lett. 2008, 18, 5631-5634; Hyodo, M.; et al., Tetrahedron 2006, 62, 3089-3094). Two analogs with a non-phosphate backbone have been prepared, one has a methylphosphonate (Shanahan, C. A.; et al., Biochemistry 2013, 52, 365-377), the other a carbamate (Kline, T.; et al., Nucleosides Nucleotides Nucl. Acids 2008, 27, 1282-1300), but each lacks a 2'-hydroxyl group. An analog with a 2'-fluoro in place of the 2'-hydroxyl, with a phosphate backbone, was reported most recently (Zhou, J.; et al., Biorganic & Medicinal Chemistry 2013, 21, 4396-4404). The work described herein below included the preparation of c-di-GMP analogs with urea or urea related backbone linkages should be stable to bacterial phosphodiesterases.

The syntheses start with introduction of nitrogen atoms to the guanosine 3' and 5' positions. The first steps include the preparation of the 5'-azido-5'-deoxy derivative 3, as shown in Scheme 1. The N²-dimethylformamidine (dmf) derivative of guanosine, 1, was prepared by standard methods as described herein. Preparation of 2 and 3 followed procedures reported for guanosine (McGee, D. P. C.; et al., Can. J. Chem. 1986, 64, 1885-1889; Dean, D. K., Synth. Commun. 2002, 32, 1517-1521). The major differences were that heating was not required for reaction of 2 with sodium azide, and that 3 was readily isolated simply by addition of methanol to the reaction mixture. The N²-dmf group has been shown to be essential for the reaction of guanosine with α-acetoxyisobutyryl bromide (He, G.- X.; et al., Tetrahedron Lett. 1995, 36, 6991-6994). The reaction of 3 proceeded analogously to that reported for 1, with no degradation of the azido group under the acidic reaction conditions. In addition to the desired product, 4, a small amount of the 2'-Br isomer was produced, in the ratio of 92:8. These isomers were not separable by chromatography, but 4 was readily crystallized from methylene chloride, which efficiently removed the 2'-Br isomer. No chromatography was required for the preparation of compounds 1-4, so that these reactions were conveniently carried out starting with 20 g of guanosine to give 4 in an overall yield of 38%.

The conversion of 4 to the 3'-amino-5'-azido derivative 9, shown in Scheme 2, proceeded analogously to the preparation of 3'-amino-3'-deoxyguanosine reported by Zhang, although by using extensively altered conditions, and some reagents, the reaction times were significantly reduced (Zhang, L.; et al., Helv. Chim. Acta 2003, 86, 703-710). Catalytic DMAP in methanol with a few equiv of TEA effected clean removal of the acetyl group from 4. The reaction of 5 with benzylisocyanate in acetonitrile then proceeded in 2 h to give 6. After investigating numerous reagents for cyclization to 7, tBuONa in THF was found to give complete conversion in 45 min. Saponification of 7 to 8 by addition of 10 N NaOH to a methanol solution of 7 proceeded in 2 h. It is somewhat surprising that the N²-dmf group survived these strongly basic conditions with only minimal loss. After neutralization of the reaction mixture, 8 was isolated by extraction. The steps from 4 to 8 were carried out in one flask, without isolation of intermediates, and 8 did not need purification before conversion to 9.

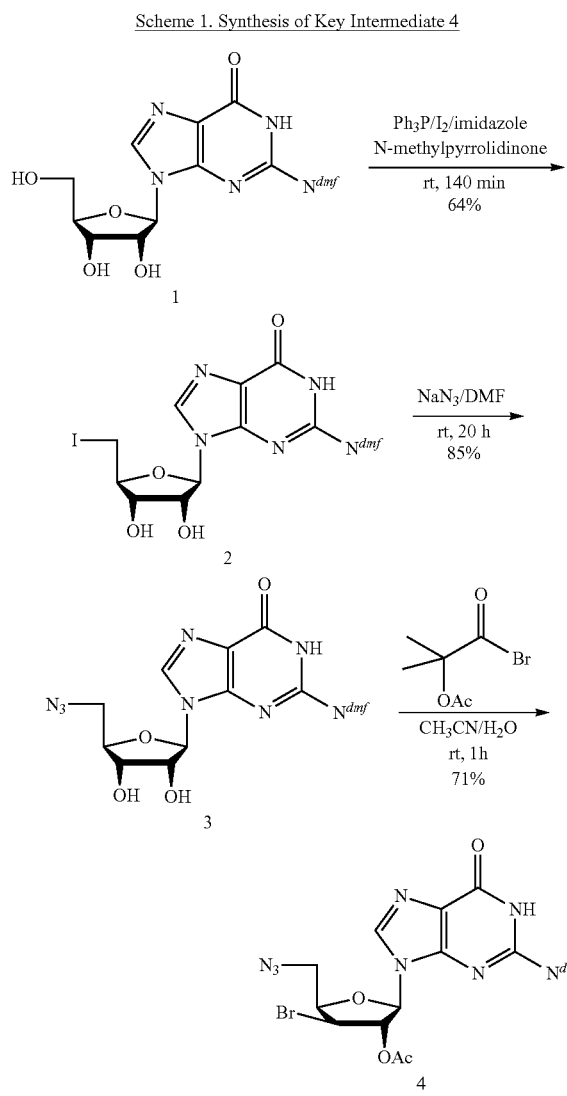

Scheme 1. Synthesis of Key Intermediate 4

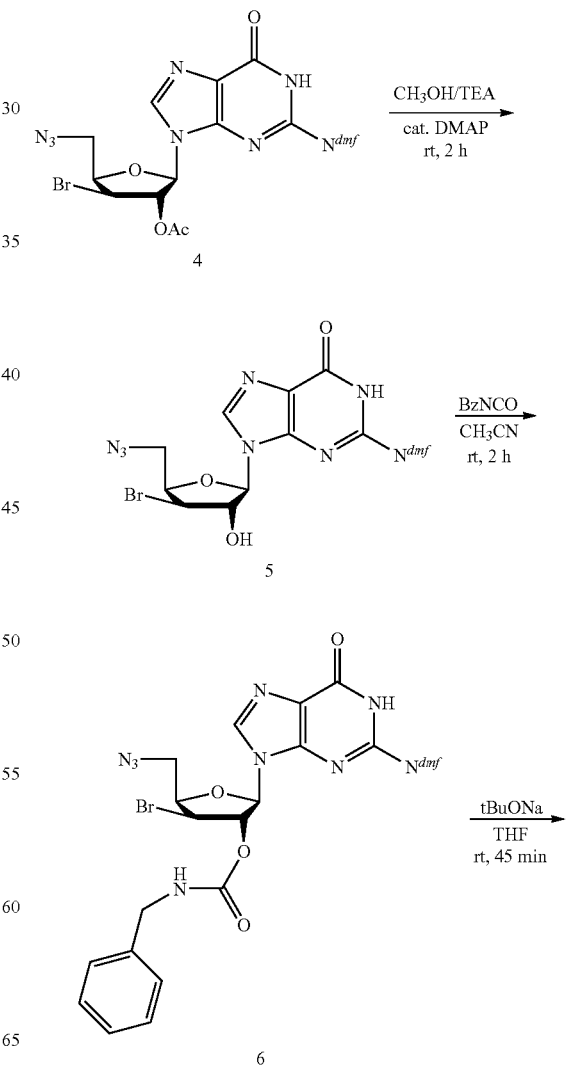

Scheme 2. Synthesis of 3'-amino-5'-azido derivative 9

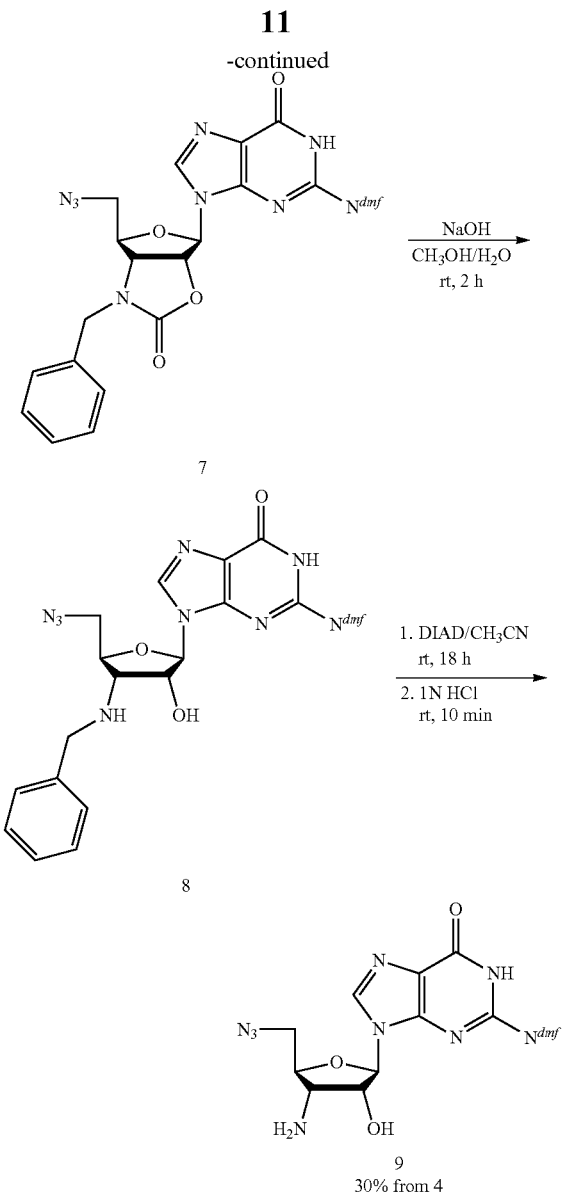

Because of the 5'-azide it was not possible to use reduction to debenzylate the 3'-amino group in 8, and instead oxidation using diisopropylazodicarboxylate (DIAD) was employed (Kroutil, J.; et al., Synthesis 2004, 446-450). This is a slow reaction that required the reaction to proceed overnight to give the corresponding imine (not shown). Hydrolysis to 9 was effected using 1 N HCl, within ten minutes, again with minimal loss of the $N^2$-dmf group. After neutralization of the reaction mixture with NaHCO$_3$, 9 was isolated by extraction, in this case remaining in the aqueous phase while excess reagent was removed in the organic phase. The purification of 9 was carried out by reversed phase chromatography using 10 mM aqueous ammonium bicarbonate and acetonitrile, to give 9 in a yield of 30% from 4. Solutions of 9 should not be allowed to stand for long periods of time in the ammonium bicarbonate eluant, as the $N^2$-dmf group is slowly hydrolyzed under these mild conditions, even though it survives limited time treatment with NaOH or HCl.

The derivatization of 9 for synthesis of the cyclic dimers required protection of the 2'-hydroxyl, conveniently done by reaction with tert-butyldimethylsilyl chloride, as shown in Scheme 3. Addition of the TBS group makes 10 again amenable to silica chromatography, and all of the subsequent intermediates were purified on silica using gradients of methanol (with 0.5% TEA for those with a free amino group or the acid labile monomethoxytrityl group) and methylene chloride. The strategy for synthesis of the linear and cyclic dimers was to elaborate the 3'-amino group into an isothiocyanate, and to couple this to a 5'-amino group obtained by Staudinger reduction of the 5'-azide. The 3'-isothiocyanate is stable to silica chromatography, so that intermediates 11 and 14 are easily handled, but it does react well with the 5'-amino group. Thus the 5'-azide functions as a stable masked amino group that can be converted to the amine without harming the 3'-isothiocyanate of 14.

Scheme 3. Synthesis of the linear dimer 14

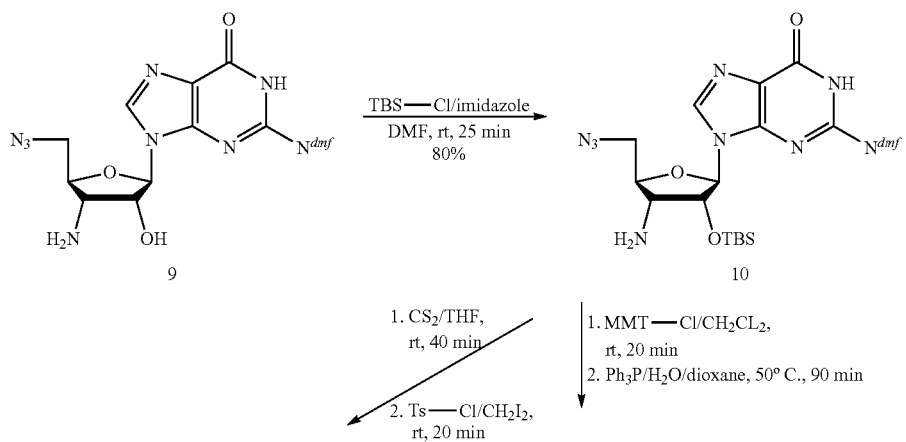

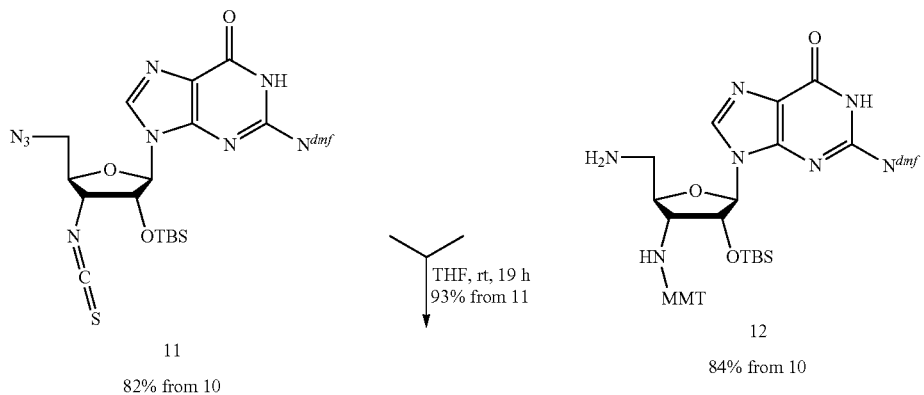

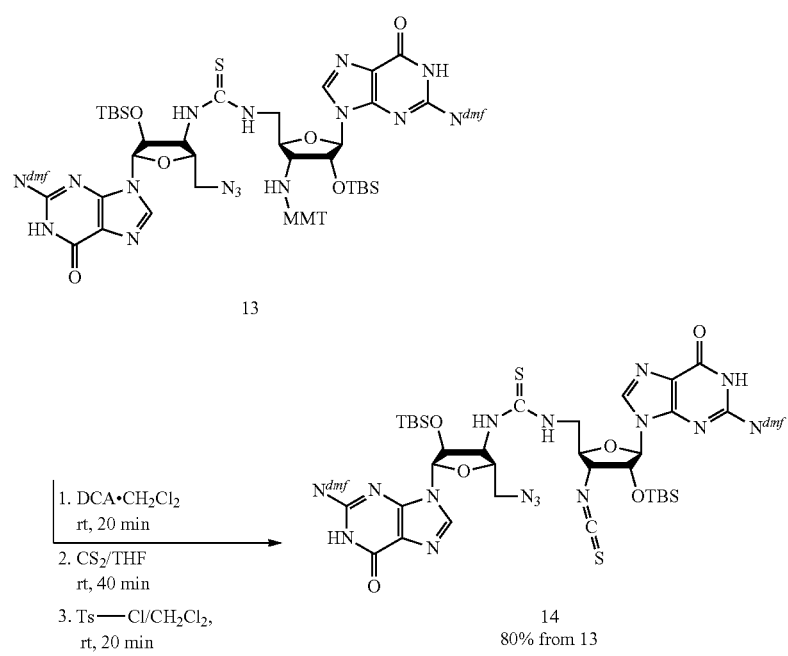

Formation of the 3'-isothiocyanate derivative 11 was carried out by reaction of 10 with carbon disulfide followed by reaction of the resulting dithiocarbamate (not shown) with tosyl chloride or benzenesulfonyl chloride (Wong, R.; et al., J. Org. Chem. 2007, 72, 3639-3971). This was done as a two step procedure using a ten fold excess of $CS_2$ in the first step, which was readily removed on a rotary evaporator before reaction with the sulfonyl chloride. The 5'-amino nucleoside 12 was obtained by Staudinger reduction after protection of the 3'-amino group of 10 by reaction with monomethoxytrityl chloride. Condensation of 11 and 12 in THF at room temperature gave clean conversion to the linear dimer 13 within 17 h in 93% yield. The monomethoxytrityl group was removed using DCA and the amino group converted to an isothiocyanate to give 14 by the same two step procedure used for preparation of 11.

Scheme 4. Syntheses of thiourea 16 and urea 17

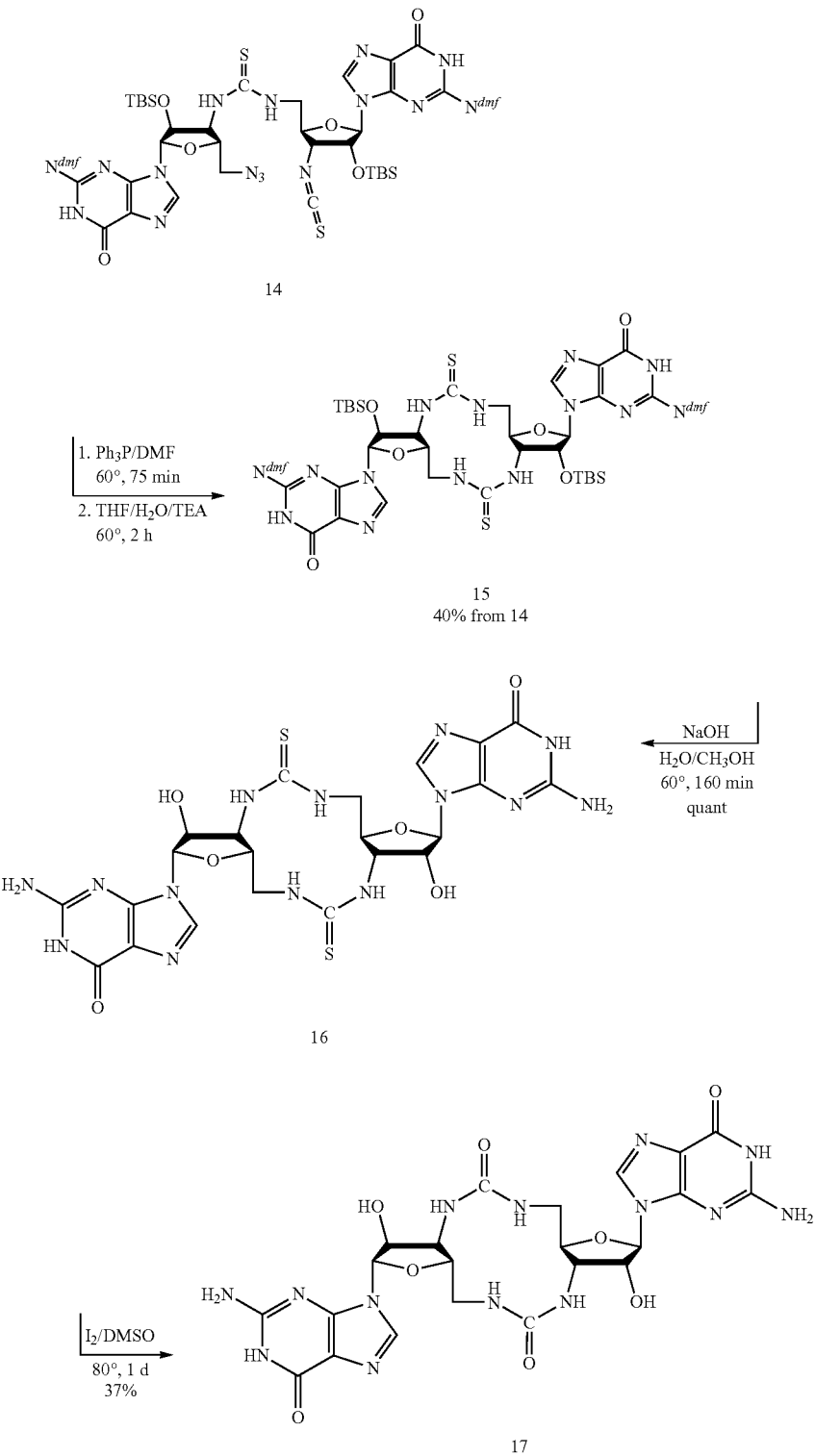

Cyclization of the linear dimer 14 to the cyclic dimer 15 was effected by a two step sequence involving reaction of 14 with triphenyl phosphine to give the azine (not shown, but sufficiently stable to be clearly visibly by LC-MS), followed by dilution of the reaction mixture with THF/water/TEA, and heating at 60° C. for 2 h. Although LC-MS shows that the protected cyclic dimer 15 was the only significant product, there were a number of small impurities visible, presumably oligomers due to intermolecular reaction, even under the dilute conditions of the cyclization. It was again possible to purify 15 by silica chromatography, using a steep gradient of methanol in methylene chloride. The isolated yield for the cyclization was only 40%, presumably because of intermolecular reactions that may compete with it.

The deprotection of 15 to the cyclic thiourea 16 was effected using 2 N NaOH in methanol/water (1:1). Under these conditions the TBS groups were removed in minutes, at room temperature, while the $N^2$-dmf groups required heating at 60° C. for 2 h to effect removal, consistent with the surprising stability noted earlier. Neutralization of the reaction mixture with either 1 N HCl or with acetic acid caused precipitation of 16, which was isolated by filtration in quantitative yield. Of the many potential routes for conversion of thioureas to ureas (Sahu, S.; et al., Journal of Sulfur Chemistry 2011, 32, 171-197), reaction of 16 with DMSO and catalytic iodine, at 80° C., was employed (Mikolajczyk, M.; et al., Synthesis 1975, 114-115). This is a simple, if slow, procedure that does not involve metals or unusual conditions, and gave clean conversion to 17, in 37% yield.

The reaction of 16 with iodine, this time in DMF at room temperature with triethylamine, was also effective for preparation of the carbodiimide 18 (Ali, A. R.; et al., Tetrahedron Lett. 2010, 51, 1019-1021). Although this reaction is reported to require aryl thioureas (Ali, A. R.; 2010), it worked well for preparation of 18. The reaction of carbodiimides with amines for synthesis of guanidines is well known (Katritzky, A. R.; et al., ARKIVOC 2005, 2005, 49-87), and aqueous methylamine and aqueous ammonia gave 19a and 19b, respectively, although slowly and in modest yields.

The carbodiimide 18 proved to be sufficiently stable to be handled and purified using the same conditions used for 17 and 19a/b. All of these compounds have poor solubility in water, but are soluble in 0.1 N NaOH. Purification of each was done by RP chromatography using 0.1 N NaOH and methanol. Neutralization of the product fractions using $CO_2$ gas gave each compound as a white solid easily isolated by filtration. The preparations of 17, 18, and 19a/b were carried out on small scales only and were not optimized.

General Methods

Analytical RP HPLC was performed on a Waters 2695 system operated by Empower software, with an Atlantis C18

Scheme 5. Syntheses of carbodiimide 18 and guanidines 19a and 19b

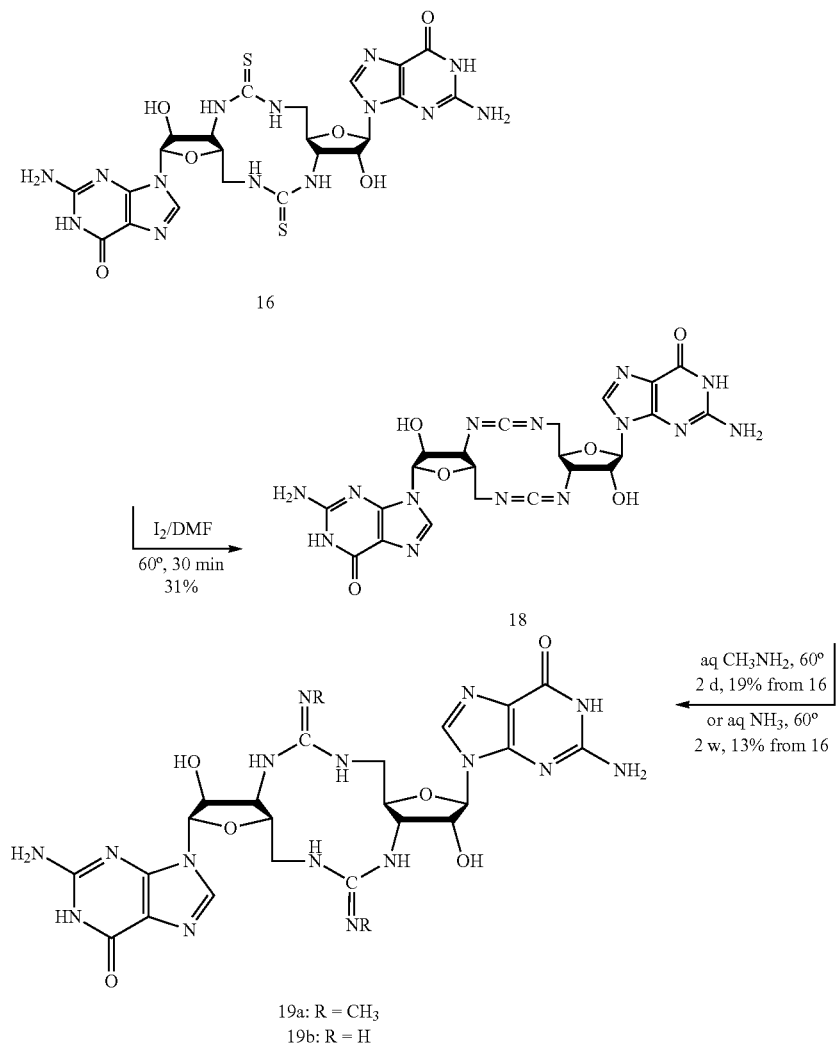

column, 4.6 mm×50 mm, 3 µm, using gradients of $CH_3CN$ and 0.1 M aq $Et_3NHOAc$ (pH 6.8) at a flow rate of 1.0 mL/min. UV spectra were from a Waters photodiode array detector connected to the HPLC. ESI-MS was acquired in negative mode using a Waters single quadrupole ZMD system operated by MassLynx software. MS data reported below were from the ESI chromatograms. Normal phase purifications were done on disposable Varian SuperFlash SF25 cartridges at 10 mL/min. The final compounds, 17-19, were purified on a Hamilton PRP C18 250×21.2 mm column using gradients of $CH_3OH$ and 0.1 N NaOH at a flow rate of 6 ml/min. All NMR spectra were acquired on a Varian VNMRS 500 MHz spectrometer in the solvents specified at 25° C., unless otherwise indicated. Spectra acquired at 25° C. were referenced to the solvents, and those acquired at higher temperatures were referenced indirectly to DSS.

Preparation of Compound 1.

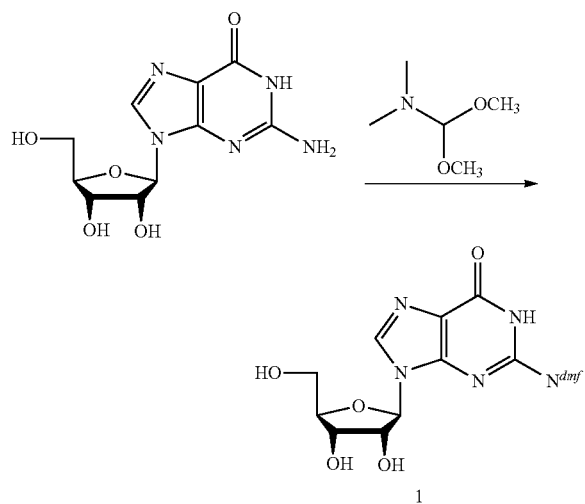

To guanosine monohydrate (21.1 g, 70 mmol) suspended in $CH_3OH$ (300 mL) was added dimethyl formamide dimethyl acetal (25.0 mL, 183 mmol, 2.61 equiv). After stirring 3 days, the product was collected by vacuum filtration, washed 4× with $CH_3OH$, and dried in a vacuum desiccator over KOH to give 23.38 g of 1 (69.1 mmol, 99%), which was characterized as follows: mp: >220° C.; m/z (M-H) 337.1 (calculated for $C_{13}H_{17}N_6O_5^-$: 337.1); UV $\lambda_{max}$ 297 nm; $^1$H NMR (DMSO) 25° C.: δ 11.32 (br, 1H), 8.53 (s, 1H), 8.03 (s, 1H), 5.79 (d, J=6 Hz, 1H), 5.40 (d, J=6 Hz, 1H), 5.17 (d, J=6 Hz, 1H), 5.02, (t, J=6 Hz, 1H), 4.53-4.43 (m, 1H), 4.16-4.06 (m, 1H), 3.95-3.85 (m, 1H), 3.66-3.60 (m, 1H), 3.57-3.51 (m, 1H), 3.15 (s, 3H), 3.03 (s, 3H); $^{13}$C NMR (DMSO) 25° C.: δ 158.0, 157.6, 157.3, 150.0, 137.0, 119.8, 86.7, 85.4, 73.8, 70.5, 61.5, 40.7, 34.6.

Preparation of Compound 2.

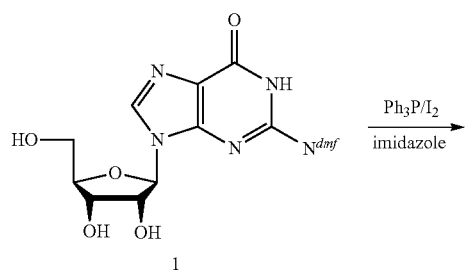

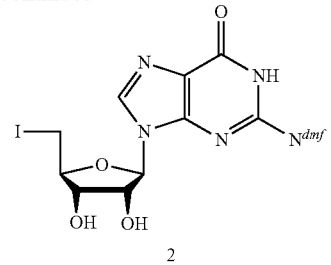

To 1 (17.76 g, 52.5 mmol) suspended in $CH_3CN$ (235 mL) was added imidazole (15.7 g, 231 mmol, 4.4 equiv) and N-methylpyrrolidinone (160 mL). The mixture was concentrated until most of the $CH_3CN$ had been removed, and a stir bar was added. Triphenylphospine (30.3 g, 116 mmol, 2.2 equiv) was added under $N_2$, and the mixture was stirred vigorously for 2 min. $I_2$ (28.0 g, 110 mmol, 2.1 equiv) was then added under $N_2$ in 4 portions. The mixture became hot and turned a clear, pale yellow. After 80 min, $H_2O$ (120 mL) was added, and the mixture was stirred vigorously for 30 min, then placed in an ice bath for 30 min. The product was collected by vacuum filtration, washed 3× with 35 mL cold $H_2O$, washed 5× with 50 mL ethyl ether, placed briefly in a vacuum desiccator to remove the ether, and then dried on a lyophilizer to give 15.0 g of 2 (33.4 mmol, 64% from 1), which was characterized as follows: mp: d 187-190° C.; m/z (M-H) 447.2 (calculated for $C_{13}H_{16}IN_6O_4^-$: 447.0); UV $\lambda_{max}$ 301 nm; $^1$H NMR (DMSO) 25° C.: δ 11.35 (br, 1H), 8.55 (s, 1H), 8.05 (s, 1H), 5.82 (d, J=6 Hz, 1H), 5.54 (d, J=6 Hz, 1H), 5.45 (d, J=5 Hz, 1H), 4.72-4.63 (m, 1H), 4.15-4.10 (m, 1H), 3.98-3.92 (m, 1H), 3.64-3.58 (m, 1H), 3.47-3.41 (m, 1H), 3.17 (s, 3H), 3.04 (s, 3H); $^{13}$C NMR (DMSO) 25° C.: δ 157.9, 157.6, 157.3, 150.1, 137.2, 119.8, 86.9, 83.6, 73.1, 72.9, 40.7, 34.7, 8.0.

Preparation of Compound 3.

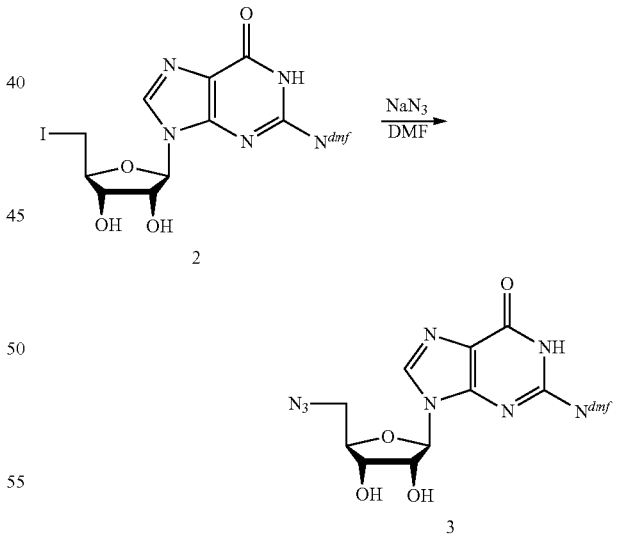

To 2 (13.16 g, 29.4 mmol) suspended in DMF (200 mL) and stirred 5 min was added $NaN_3$ (3.81 g, 58.6 mmol, 2 equiv. The suspension was loosely covered and stirred for 20 h, $CH_3OH$ (200 mL) was added, and the mixture was stirred for 30 min. The product was collected by vacuum filtration, washed 3× with 50 mL $CH_3OH$, and dried in a desiccator over KOH to give 9.10 g of 3 (25.1 mmol, 85% from 2), which was characterized as follows: mp: d 217-220° C.; m/z (M-H) 362.1 (calculated for $C_{13}H_{16}N_9O_4^-$: 362.1); UV $\lambda_{max}$ 300 nm; $^1$H NMR (DMSO) 25° C.: δ 11.34 (br, 1H), 8.57 (s, 1H), 8.04 (s, 1H), 5.83 (d, J=6 Hz, 1H), 5.54 (br, 1H), 5.37 (br, 1H), 4.61-4.55 (m, 1), 4.18-4.12 (m, 1H), 4.04-3.97 (m, 1H), 3.64-3.55 (m, 2H), 3.17, (s, 3H), 3.04 (s, 3H); $^{13}$C NMR (DMSO) 25° C.: δ 157.9, 157.6, 157.3, 150.0, 137.1, 119.8, 87.1, 82.7, 73.1, 70.8, 51.7, 40.7, 34.7.

Preparation of Compound 4.

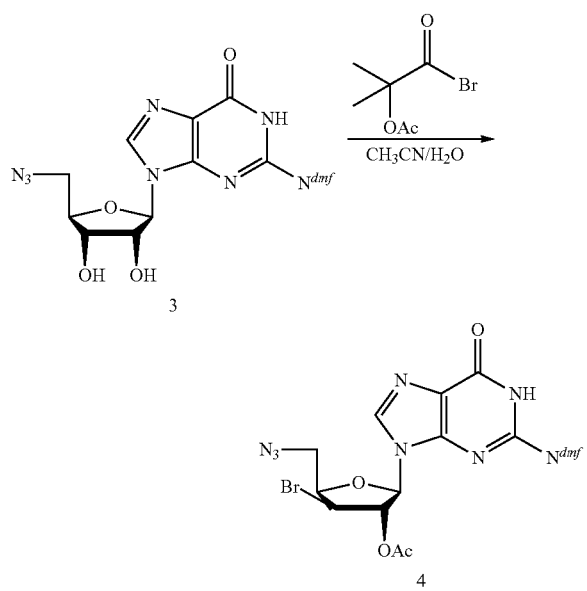

To 3 (5.67 g, 15.5 mmol) suspended in CH$_3$CN (155 mL) was added H$_2$O (0.49 mL). The flask was evacuated and refilled with N$_2$ 10× and α-acetoxy isobutyryl bromide (also known as 1-bromocarbonyl-1-methylethyl acetate) (7.6 mL, 52.1 mmol, 3.36 equiv) was added by syringe over 1 min while stirring. After 1 h, the mixture was poured into H$_2$O (155 mL) and NaHCO$_3$ (6.55 g, 78 mmol, 1.5 equiv). After 5 min, the mixture was partitioned with CH$_2$Cl$_2$ (155 mL) and the aq layer was washed with CH$_2$Cl$_2$ (55 mL). The combined organic layers were concentrated, CH$_3$CN (100 mL) was added and the mixture concentrated to a foam using CH$_2$Cl$_2$ (50 mL) for the final concentration. The foam was dissolved in CH$_3$OH (42 mL) from which the crude product crystallized in a few minutes. After 30 min of chilling in an ice bath, the crude product containing about 1% of the 2'-Br-3'-OAc isomer was collected by vacuum filtration, washed 3× with 7 mL cold CH$_3$OH, and dried in a vacuum desiccator over KOH to give 5.86 g of crude 4 (12.5 mmol, 81% from 3). Crude 4 was recrystallized by dissolving it in CH$_2$Cl$_2$ (150 mL), concentrating it to about 20 mL, and chilling it in an ice bath for 1 h. The pure product was collected by vacuum filtration, washed 3× with cold CH$_2$Cl$_2$, and dried in a vacuum desiccator over KOH to give 4.60 g of a 1$^{st}$ crop and 0.44 g of a 2$^{nd}$ crop of pure 4 (11.04 mmol, 71% from 3), which was characterized as follows: mp: d 160-162° C.; m/z (M-H) 465.9 (calculated for C$_{15}$H$_{17}$BrN$_9$O$_4^-$: 466.1); UV λ$_{max}$ 300 nm; $^1$H NMR (DMSO) 25° C.: δ 11.42 (br, 1H), 8.60 (s, 1H), 7.99 (s, 1H), 6.08 (ap t, J=3 Hz, 1H, H2'), 6.02 (d, J=3 Hz, 1H, H1'), 4.89-4.84 (m, 1H, H3'), 4.47-4.42 (m, 1H, H4'), 3.90-3.83 (m, 1H, H5' or H5"), 3.66-3.59 (m, 1H, H5' or H5"), 3.15 (s, 3H), 3.05 (s, 3H), 2.12 (s, 3H); $^{13}$C NMR (DMSO) 25° C.: δ 169.9, 158.8, 158.1, 158.0, 150.1, 137.0, 119.9, 87.3, 81.2, 79.3, 53.1, 50.3, 41.2, 35.1, 20.8. The 3'-Br and 2'-Br isomers of 4 were identified from analysis of the connectivities of the crosspeaks in GCOSY 2D NMR, and a comparison of crosspeak intensities in NOESY zq 2D NMR, shown with the pages of spectra below.

Preparation of Compound 5.

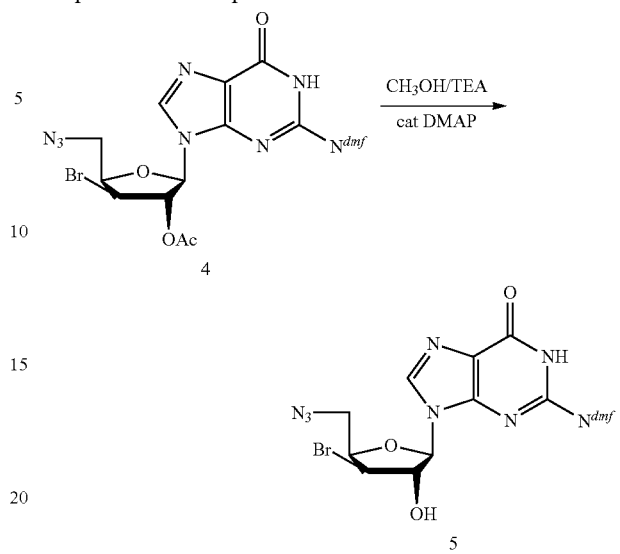

To 4 (7.02 g, 15.0 mmol) suspended in CH$_3$OH (250 mL) was added DMAP (90 mg, 0.75 mmol, 0.05 equiv) and TEA (6.0 mL, 45 mmol, 3 equiv). The mixture was stirred for 2 h, and the clear solution was concentrated and dried by evaporation of CH$_3$CN 4×. The resulting solid was dried in a desiccator overnight over KOH, and used in the next step without further purification. A sample of 5 from another preparation was crystallized from the reaction mixture upon cooling, and characterized as follows: mp: d 151-153° C.; m/z (M-H) 423.9 (calculated for C$_{13}$H$_{15}$BrN$_9$O$_3^-$: 424.0); UV λ$_{max}$ 301 nm; $^1$H NMR (DMSO) 25° C.: δ 11.40 (s, 1H), 8.57 (s, 1H), 8.05 (s, 1H), 6.47 (d, J=6 Hz, 1H), 5.77 (d, J=5 Hz, 1H), 4.99-4.94 (m, 1H), 4.60-4.56 (m, 1H), 4.46-4.40 (m, 1H), 3.86-3.79 (m, 1H), 3.62-3.55 (m, 1H), 3.14 (s, 3H), 3.03 (s, 3H); $^{13}$C NMR (DMSO) 25° C.: δ 158.7, 158.2, 158.1, 150.6, 137.4, 120.4, 88.3, 80.3, 78.3, 53.8, 41.4, 35.4.

Preparation of Compound 6.

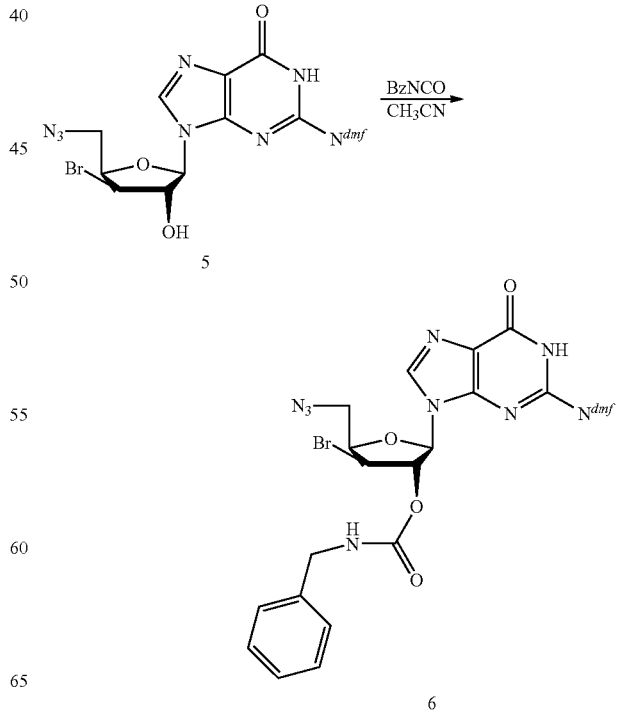

To the solid residue of 5 from above, scraped and loosened from the sides of the flask, and then suspended in CH$_3$CN (150 mL), was added benzyl isocyanate (2.25 mL, 18.3 mmol, 1.2 equiv) and TEA (0.51 mL, 3.75 mmol, 0.25 equiv). The mixture was stirred for 2 h, concentrated to a foam, dried in a desiccator overnight over KOH, and used in the next step without further purification. A sample of 6 from another preparation was purified for analysis on silica gel using CH$_3$OH and CH$_2$Cl$_2$, and characterized as follows: m/z (M-H) 557.2 (calculated C$_{21}$H$_{22}$BrN$_{10}$O$_4{}^-$: 557.1); UV $\lambda_{max}$ 302 nm; $^1$H NMR (DMSO) 25° C.: δ 11.43 (s, 1H), 8.59 (s, 1H), 8.16 (t, J=6 Hz, 1H), 8.01 (s, 1H), 7.32-7.17 (m, 5H), 6.06 (ap t, J=4 Hz, 1H), 6.01 (d, J=4 Hz, 1H), 4.89-4.82 (m, 1H), 4.50-4.42 (m, 1H), 4.19 (d, J=6 Hz, 2H), 3.93-3.87 (m, 1H), 3.67-3.61 (m, 1H), 3.07 (s, 3H), 3.03 (s, 3H); $^{13}$C NMR (DMSO) 25° C.: δ 159.0, 158.9, 158.2, 155.3, 150.2, 139.7, 136.9, 129.0, 127.9, 127.6, 120.4, 87.4, 81.5, 79.5, 53.6, 50.6, 44.6, 41.3, 35.6.

Preparation of Compound 7.

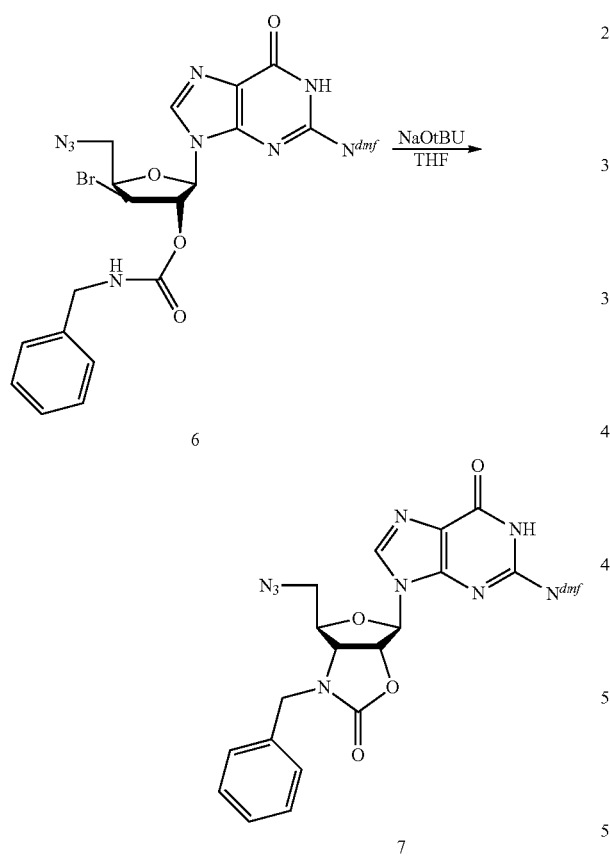

To the solid residue of 6 from above dissolved in THF (150 mL), was added sodium tert-butoxide (4.32 g, 45 mmol, 3 equiv). The mixture was stirred for 45 min, concentrated to a powder, the residue dried in a desiccator overnight over KOH, and used in the next step without further purification. A sample from another preparation of 7 was purified for analysis on silica gel using CH$_3$OH and CH$_2$Cl$_2$, and characterized as follows: m/z (M-H) 477.0 (calculated for C$_{21}$H$_{21}$N$_{10}$O$_4{}^-$: 477.2); UV $\lambda_{max}$ 303 nm; $^1$H NMR (DMSO) 25° C.: δ 11.42 (br, 1H), 8.53 (s, 1H), 8.02 (s, 1H), 7.44-7.31 (m, 5H), 6.28 (d, J=3 Hz, 1H), 5.89-5.84 (m, 1H), 4.66-4.59 (m, 1H), 4.43-4.33 (m, 3H), 3.46-3.41 (m, 1H), 3.37-3.31 (m, 1H), 3.03 (s, 3H), 3.02 (s, 3H); $^{13}$C NMR (DMSO) 25° C.: δ 159.0, 158.2, 158.1, 156.8, 150.0, 138.3, 136.5, 129.5, 128.7, 128.6, 120.6, 89.4, 83.9, 79.9, 61.2, 52.1, 46.9, 41.4, 35.3.

Preparation of Compound 8.

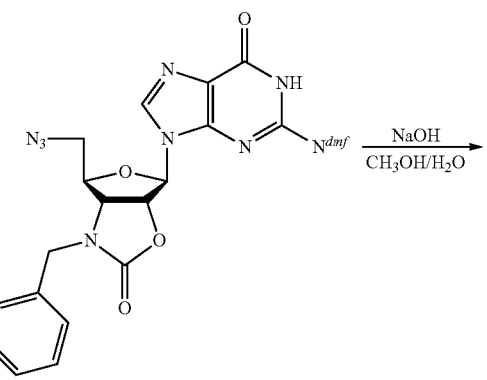

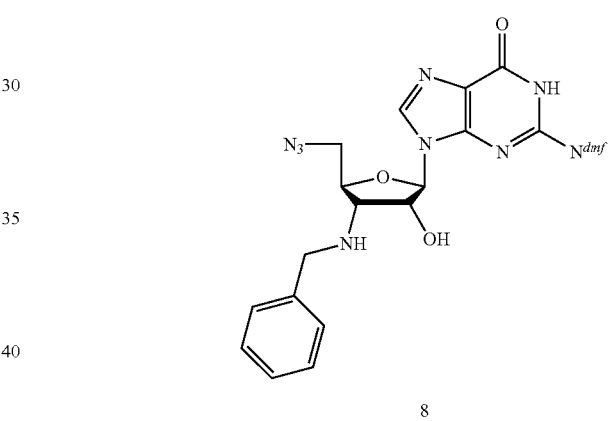

To the solid residue of 7 from above was added CH$_3$OH (90 mL). To this mixture, chilled in an ice bath, was slowly added 10 N NaOH (60 mL). The ice bath was removed, the mixture was stirred for 2 h, and then chilled again. The solution was neutralized over 1 min with cold 4 N HCl (150 mL) to pH 8. The product was partitioned with 150 mL CH$_2$Cl$_2$, and the aq layer was washed with 4×75 mL CH$_2$Cl$_2$. The combined organic layers were concentrated to a foam, dried in a desiccator overnight over KOH, and used in the next step without further purification. A sample from another preparation of 8 was purified for analysis on silica gel using CH$_3$OH and CH$_2$Cl$_2$, and characterized as follows: m/z (M-H) 451.2 (calculated for C$_{20}$H$_{23}$N$_{10}$O$_3{}^-$: 451.2); UV $\lambda_{max}$ 303 nm; $^1$H NMR (DMSO) 25° C.: δ 11.33 (br, 1H), 8.55 (s, 1H), 7.95 (s, 1H), 7.37-7.19 (m, 5H), 5.96 (br, 1H), 5.89 (d, J=2 Hz, 1H), 4.60-4.55 (m, 1H), 3.98-3.91 (m, 1H), 3.85-3.69 (m, 2H), 3.64-3.58 (m, 1H), 3.53-3.47 (m, 1H), 3.45-3.39 (m, 1H), 3.11 (s, 3H), 3.02 (s, 3H); $^{13}$C NMR (DMSO) 25° C.: δ 158.6, 158.3, 158.0, 150.3, 141.2, 137.5, 128.9, 128.6, 127.4, 120.5, 89.8, 82.0 72.5, 60.8, 52.6, 51.9, 41.3, 35.4.

Preparation of Compound 9.

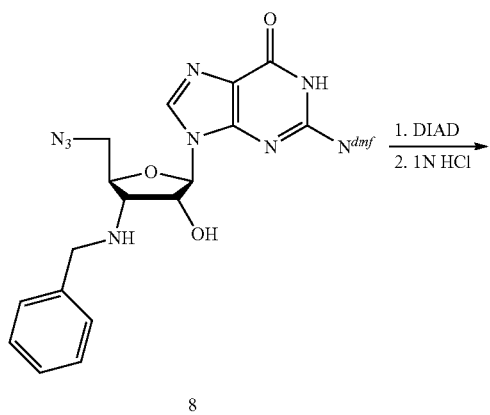

To the solid residue of 8 from above, partially dissolved in CH$_3$CN (150 mL), was added diisopropyl azodicarboxylate (DIAD, 15 mL, 75 mmol, 10 equiv). The mixture was stirred for 18 h. The resulting intermediate imine was hydrolyzed by addition of 1 N HCl (30 mL). After 10 min, the solution was diluted with 30 mL of H$_2$O, and then neutralized with 60 mL of 0.5 M NaHCO$_3$ to give pH 8. The mixture was partitioned with 200 mL of CH$_2$Cl$_2$ to remove an impurity which would otherwise later co-elute with the product, then washed again with 2×50 mL of CH$_2$Cl$_2$. The combined organic layers were backwashed with 3×5 mL of H$_2$O. The aq layers, which contained some solid, were combined and partially concentrated to remove all organic solvent. The mixture was filtered and purified by preparative RP chromatography on a Delta-Pak C18 (40×100 mm) column using a gradient of 0 to 25% CH$_3$CN in 0.02 M aq NH$_4$HCO$_3$ in 45 min at 10 mL/min. Fractions containing pure product were combined and lyophilized, to give 1.64 g of 9 (4.53 mmol, 30% from 4, which was characterized as follows: m/z (M-H) 361.2 (calculated for C$_{13}$H$_{17}$N$_{10}$O$_3^-$: 361.1); UV $\lambda_{max}$ 300 nm; $^1$H NMR (DMSO) 25° C.: δ 8.58 (s, 1H), 7.95 (s, 1H), 5.84 (d, J=2 Hz, 1H), 4.32-4.27 (m, 1H), 3.82-3.75 (m, 1H), 3.67-3.60 (m, 1H), 3.55-3.47 (m, 2H), 3.15 (s, 3H), 3.02 (s, 3H); $^{13}$C NMR (DMSO) 25° C.: δ 158.7, 158.3, 157.9, 150.3, 137.4, 120.4, 89.4, 83.6, 75.1, 54.9, 52.4, 41.4, 35.4.

Preparation of Compound 10.

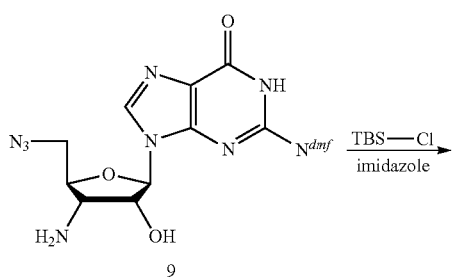

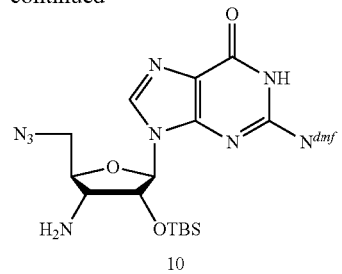

To 9 (1.07 g, 3.0 mmol) suspended in DMF (30 mL) was added imidazole (1.2 g, 18 mmol) and tert-butyldimethylchlorosilane (1.4 g, 9 mmol). After 25 min the mixture was diluted by addition of CH$_2$Cl$_2$ (30 mL) and the mixture partitioned with 0.5 M NaHCO$_3$ (100 mL), washed with 3×10 mL CH$_2$Cl$_2$. The organic layers were concentrated and the DMF removed using a vacuum pump. The residue was dissolved in CH$_2$Cl$_2$ and applied to a silica column (80 g), then eluted using a gradient of 0 to 20% CH$_3$OH (containing 0.5% TEA) to CH$_2$Cl$_2$ in 30 min. The product eluted as a sharp peak at about 50% of the gradient. Concentration of product fractions gave 1.13 g of 10 (2.4 mmol, 80% from 9), which was characterized as follows: m/z (M-H) 475.2 (calculated for C$_{19}$H$_{31}$N$_{10}$O$_3$Si$^-$: 475.2); UV $\lambda_{max}$ 302 nm; $^1$H NMR (DMSO) 25° C.: δ 11.36 (br, 1H), 8.55 (s, 1H), 7.98 (s, 1H), 5.85 (d, J=2 Hz, 1H), 4.39-4.36 (m, 1H), 3.84-3.78 (m, 1H), 3.69-3.60 (m, 2H), 3.51-3.46 (m, 1H), 3.12 (s, 3H), 3.03 (s, 3H), 0.85 (s, 9H), 0.03 (s, 3H), 0.01 (s, 3H); $^{13}$C NMR (DMSO) 25° C.: δ 158.6, 158.3, 158.0, 150.1, 137.2, 120.4, 89.4, 83.6, 77.4, 54.9, 52.3, 41.4, 35.3, 26.3, 18.5, −4.2, −4.3.

Preparation of Compound 12.

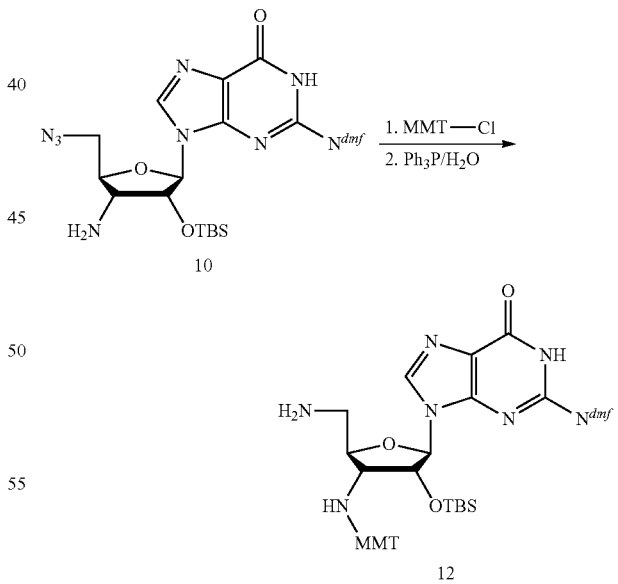

To 10 (0.86 g, 1.8 mmol) dissolved in CH$_2$Cl$_2$ (18 mL) was added TEA (0.63 mL, 4.5 mmol) and 4-methoxytrityl chloride (1.4 g, 4.5 mmol). After twenty minutes the reaction mixture was partitioned with 0.5 M NaHCO$_3$ (50 mL) and washed with 2×5 mL portions of CH$_2$Cl$_2$. The CH$_2$Cl$_2$ layers were concentrated and the residue applied to a silica column (80 g), then eluted using a gradient of 0 to 13% CH$_3$OH (containing 0.5% TEA) to $CH_2Cl_2$ in 30 min. The product eluted sharply near 50% of the gradient. Concentration of the product fractions gave 1.29 g (1.7 mmol, 96%), which was characterized as follows: m/z (M-H) 747.7 (calculated for $C_{39}H_{47}N_{10}O_4Si^-$: 747.9); UV $\lambda_{max}$ 304 nm; $^1$H NMR (DMSO) 25° C.: δ 11.37 (s, 1H), 8.40 (s, 1H), 7.85 (s, 1H), 7.46-7.38 (m, 4H), 7.29-7.12 (m, 8H), 6.80-6.76 (m, 2H), 5.87 (d, J=3 Hz, 1H), 3.84-3.78 (m, 1H), 3.77-3.71 (m, 1H), 3.65 (s, 3H), 3.54-3.48 (m, 1H), 3.39-3.34 (m, 1H), 3.12-3.04 (m, 1H), 3.07 (s, 3H), 3.02 (s, 3H), 0.81 (s, 9H), −0.11 (s, 3H), −0.16 (s, 3H); $^{13}$C NMR (DMSO) 25° C.: δ 158.4, 158.3, 158.2, 157.9, 149.8, 146.9, 138.1, 136.8, 130.4, 128.8, 128.6, 127.2, 120.7, 113.9, 88.4, 81.8, 74.7, 70.2, 56.8, 55.7, 51.9, 41.4, 35.3, 26.3, 18.3, −4.0, −4.2. To this residue dissolved in dioxane (15 mL) was added $H_2O$ (2 mL), TEA (0.26 mL, 1.9 mmol) and triphenylphosphine (1.8 g, 6.8 mmol). The reaction was maintained in an oil bath at 50° C. for 90 min. The reaction was cooled, concentrated, and the residue applied to a silica column (80 g), then eluted using a gradient of 0 to 25% $CH_3OH$ (containing 0.5% TEA) to $CH_2Cl_2$ in 20 min. The product eluted as a broad peak at 55% of the gradient. Concentration of the product fractions gave 1.1 g of 12 (1.52 mmol, 84% from 10), which was characterized as follows: m/z (M-H) 721.4 (calculated for $C_{39}H_{49}N_8O_4Si^-$: 721.4); UV $\lambda_{max}$ 304 nm; $^1$H NMR (DMSO) 25° C.: Q 8.38 (s, 1H), 8.15 (s, 1H), 7.48-7.37 (m, 4H), 7.31-7.09 (m, 8H), 6.78-6.70 (m, 2H), 5.80 (s, 1H), 3.79-3.71 (m, 1H), 3.64 (s, 3H), 3.10-3.04 (m, 2H), 3.06 (s, 3H), 3.01 (s, 3H), 2.94-2.84 (m, 1H), 2.88-2.83 (m, 2H), 0.80 (s, 9H), −0.12 (s, 3H), −0.15 (s, 3H); $^{13}$C NMR (DMSO) 25° C.: δ 158.4, 158.2, 157.8, 149.7, 147.2, 147.1, 138.3, 137.4, 130.3, 128.8, 128.6, 127.1, 120.7, 113.8, 88.3, 84.2, 75.3, 70.1, 55.9, 55.6, 42.7, 41.3, 35.2, 26.3, 18.3, −3.8, −4.3.

Preparation of Compound 11.

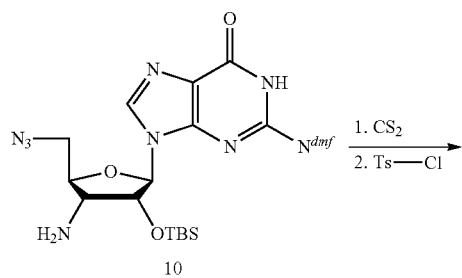

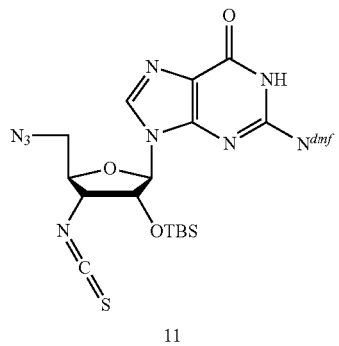

11

To 10 (1.2 g, 2.5 mmol) dissolved in THF (25 mL) was added TEA (0.38 mL, 2.75 mmol) and carbon disulfide (1.5 mL, 25 mmol). After 40 min the mixture was concentrated. To the residue dissolved in $CH_2Cl_2$ was added TEA (0.76 mL, 5.5 mmol) and tosyl chloride (525 mg, 2.75 mmol). After 20 min the mixture was partitioned with 0.5 M $NaHCO_3$ (50 mL), washed with 2×10 mL portions of $CH_2Cl_2$. The $CH_2Cl_2$ layers were concentrated and the residue applied to a silica column (80 g), then eluted using a gradient of 0 to 10% $CH_3OH$ in $CH_2Cl_2$ in 30 min. The product eluted as a sharp peak at 55% of the gradient. Concentration of the product fractions gave 1.04 g of 11 (2.04 mmol, 82% from 10), which was used for preparation of 13, although trace amounts of tosyl impurities were visible in the $^1$H NMR. A pure sample of 11 was prepared analogously on a smaller scale using 2 eq of benzenesulfonyl chloride to give 11 in a yield of 73% from 10, which was characterized as follows: m/z (M-H) 475.2 (calculated for $C_{19}H_{31}N_{10}O_3Si^-$: 475.2); UV $\lambda_{max}$ 302 nm; $^1$H NMR (DMSO) 25° C.: δ 11.36 (br, 1H), 8.55 (s, 1H), 7.98 (s, 1H), 5.85 (d, J=2 Hz, 1H), 4.39-4.36 (m, 1H), 3.84-3.78 (m, 1H), 3.69-3.60 (m, 2H), 3.51-3.46 (m, 1H), 3.12 (s, 3H), 3.03 (s, 3H), 0.85 (s, 9H), 0.03 (s, 3H), 0.01 (s, 3H); $^{13}$C NMR (DMSO) 25° C.: δ 158.6, 158.3, 158.0, 150.1, 137.2, 120.4, 89.4, 83.6, 77.4, 54.9, 52.3, 41.4, 35.3, 26.3, 18.5, −4.2, −4.3.

Preparation of Compound 13.

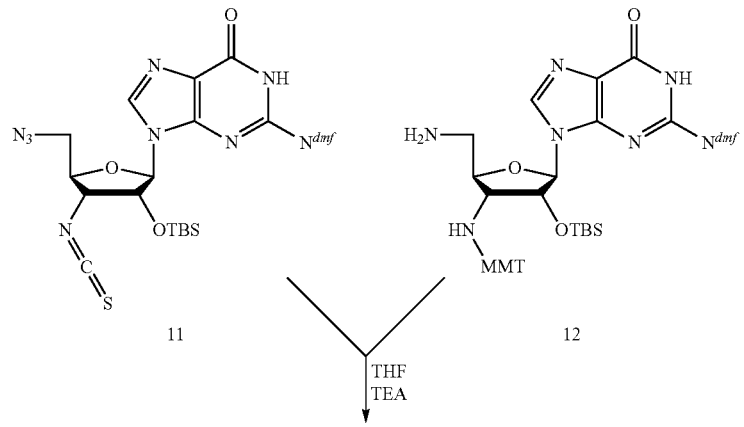

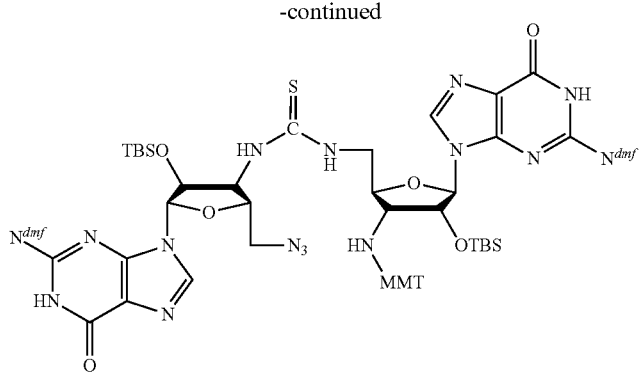

13

To 11 (1.1 g, 1.5 mmol) and 12 (0.94 g, 1.8 mmol) dissolved in THF (18 mL) was added TEA (0.21 mL, 1.5 mmol). After 19 h the mixture was concentrated and the residue applied to a silica column (80 g), then eluted using a gradient of 0 to 15% CH$_3$OH (containing 0.5% TEA) to CH$_2$Cl$_2$ in 25 min. The product eluted as a broad peak at 50% of the gradient. Concentration of the product fractions gave 1.8 g of 13 (1.4 mmol, 93% from 11), which was characterized as follows: m/z (M-H) 1239.7 (calculated for C$_{59}$H$_{79}$N$_{18}$O$_7$SSi$_2^-$: 1239.6); UV λ$_{max}$ 304 nm; $^1$H NMR (DMSO) 25° C.: δ 11.37 (s, 2H), 8.75 (s, 1H), 8.33 (s, 1H), 8.02 (s, 1H), 7.86 (s, 1H), 7.70 (br, 1H), 7.58 (br, 1H), 7.52-7.40 (m, 4H), 7.35-7.10 (m, 8H), 6.81-6.74 (m, 2H), 5.91 (s, 1H), 5.80 (d, J=3 Hz, 1H), 5.34-5.17 (m, 1H), 4.85-4.71 (m, 1H), 4.42-4.24 (m, 1H), 4.10-4.00 (m, 1H), 3.92-3.83 (m, 1H), 3.73-3.48 (m, 3H), 3.66 (s, 3H), 3.16-3.15 (m, 1H), 3.15 (s, 3H), 3.04 (s, 3H), 3.03 (s, 3H), 3.00 (s, 3H), 2.94-2.84 (m, 1H), 0.79 (s, 9H), 0.73 (s, 9H), -0.11 (s, 6H), -0.15 (s, 3H), -0.18 (s, 3H); $^{13}$C NMR (DMSO) 25° C.: δ 158.8, 158.4, 158.3, 158.2, 158.1, 158.0, 157.8, 150.2, 149.8, 147.2, 147.1, 139.3, 138.1, 137.4, 130.4, 128.8, 128.6, 127.1, 121.0, 120.9, 113.9, 90.7, 89.0, 81.8, 81.5, 74.5, 70.1, 58.1, 56.8, 55.6, 52.0, 49.3, 47.7, 41.4, 35.4, 35.3, 26.3, 26.2, 18.4, 18.3, -4.0, -4.3, -4.6, -4.7.

Preparation of Compound 14.

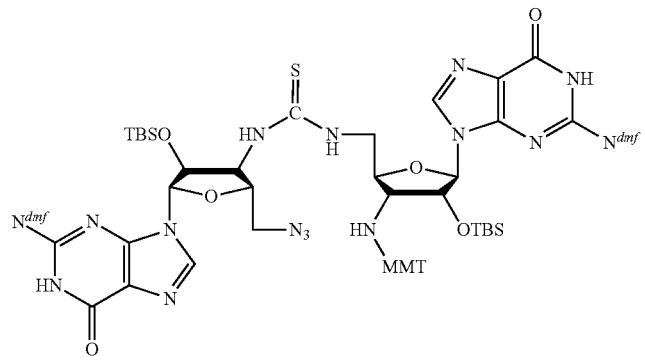

13

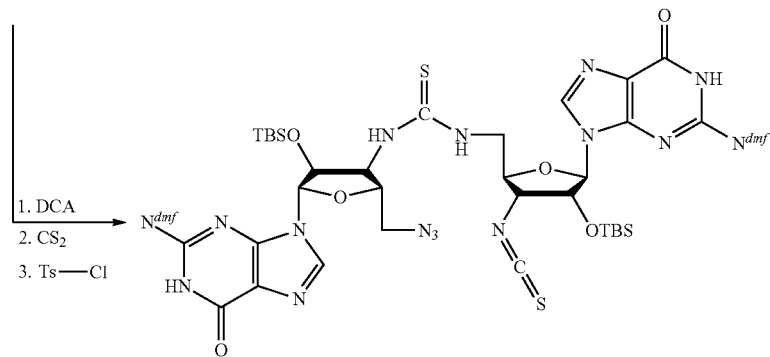

14

To 13 dissolved in CH$_2$Cl$_2$ (20 mL) was added 5% dichloroacetic acid in CH$_2$Cl$_2$ (20 mL). After twenty minutes the mixture was added to 0.5 M NaHCO$_3$ (50 mL) and CH$_3$OH (10 mL). The product separated as a gummy solid. The mixture was transferred to a separatory funnel and the layers separated. The gummy solid was dissolved in CH$_3$OH (5 mL), diluted with CH$_2$Cl$_2$ (20 mL), and partitioned with the aq layer. This was repeated two times until the gummy solid was all transferred to the organic layer. The combined organic layers were concentrated. To the residue dissolved in THF was added TEA (0.23 mL, 1.65 mmol) and carbon disulfide (0.9 mL, 15 mmol). Solid formed upon addition of carbon disulfide, that dissolved upon addition of a fraction of a mL of CH$_3$OH. After 40 min the mixture was concentrated. To the residue suspended in CH$_2$Cl$_2$ was added TEA (0.42 mL, 3 mmol) and tosyl chloride (287 mg, 1.5 mmol). All solid dissolved within 5 min. After 20 min the mixture was partitioned with 0.5 M NaHCO$_3$ (50 mL), washed with 3×10 mL portions of a mixture of CH$_3$OH and CH$_2$Cl$_2$ (1:4). The combined organic layers were concentrated and the residue applied to a silica column (80 g), then eluted using a gradient of 0 to 20% CH$_3$OH in CH$_2$Cl$_2$ in 22 min. The product eluted at 60% of the gradient. Concentration of the product fractions gave 1.18 g of 14 (1.2 mmol, 80% from 13), which was characterized as follows: m/z (M-H) 1009.5 (calculated for C$_{40}$H$_{61}$N$_{18}$O$_6$S$_2$Si$_2^-$: 1009.4); UV $\lambda_{max}$ 304 nm; $^1$H NMR (DMSO) 25° C.: δ 11.42 (s, 1H), 11.37 (s, 1H), 8.73 (s, 1H), 8.52 (s, 1H), 8.04 (s, 1H), 8.01 (s, 1H), 7.94 (br, 1H), 7.63 (br, 1H), 5.84 (d, J=5 Hz, 1H), 5.81 (br, 1H), 5.35-5.19 (m, 2H), 4.83-4.72 (m, 2H), 4.33-4.25 (m, 2H), 4.25-4.07 (m, 1H), 3.65-3.49 (m, 2H), 3.22-3.18 (m, 1H), 3.14 (s, 3H), 3.12 (s, 3H), 3.03 (s, 3H), 3.01 (s, 3H), 0.78 (s, 9H), 0.75 (s, 9H), 0.02, (s, 3H), −0.09 (br, 6H), −0.16 (s, 3H); $^{13}$C NMR (DMSO) 25° C.: δ 158.8, 158.4, 158.3, 158.2, 158.0, 153.3, 150.3, 150.2, 140.0, 138.4, 138.1, 133.5, 128.7, 124.7, 120.8, 90.8, 88.5, 81.3, 81.1, 74.6, 73.8, 60.4, 56.8, 51.9, 46.5, 41.5, 35.4, 26.2, 26.1, 18.4, 18.2, −4.4, −4.6, −4.7, −4.8.

Preparation of Compound 15.

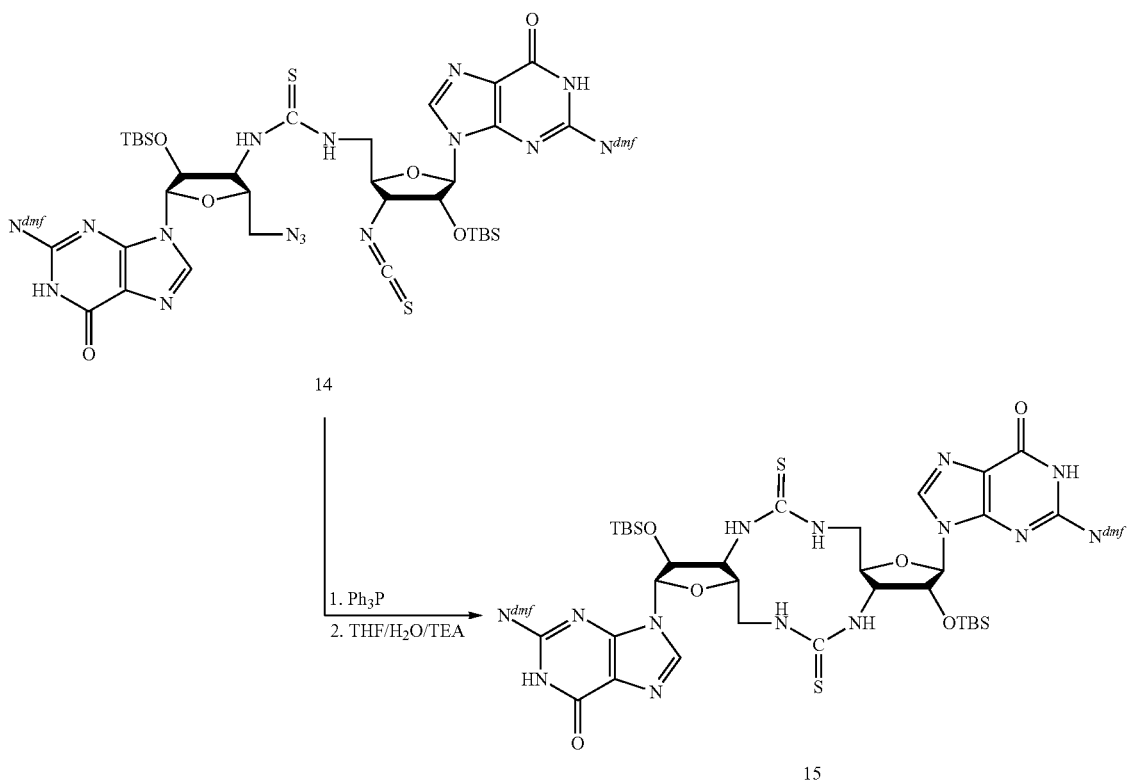

To 14 (1.14 g, 1.13 mmol) dissolved in DMF (60 mL) was added triphenylphosphine (943 mg, 3.6 mmol), and the mixture was heated at 60° C. After 75 minutes THF (48 mL), H$_2$O (12 mL) and TEA (1.2 mL) were added. After an additional two hours the mixture was concentrated and the crude product was precipitated by addition of diethyl ether (700 mL). The precipitate was dissolved in CH$_2$Cl$_2$ (with addition of a few drops of methanol) and applied to a silica column (60 g), then eluted using a gradient of 1 to 30% CH$_3$OH in CH$_2$Cl$_2$ in 21 min. The product eluted at 40% of the gradient. Concentration of the product fractions gave 440 mg of 15 (0.45 mmol, 40% from 14), which was characterized as follows: m/z (M-H) 983.5 (calculated for C$_{40}$H$_{63}$N$_{16}$O$_6$S$_2$Si$_2^-$: 983.4); UV $\lambda_{max}$ 304 nm; $^1$H NMR (DMSO) 60° C. because of aggregation: δ 11.18 (s, 2H), 8.61 (s, 2H), 8.05 (s, 2H), 7.35 (s, 2H), 5.92 (br, 2H), 4.88 (br, 2H), 4.11 (br, 3H), 3.18 (s, 6H), 3.09 (s, 6H), 0.84 (s, 18H), 0.04 (s, 6H), 0.01 (s, 6H); $^{13}$C NMR (DMSO) 60° C.: δ 159.3, 159.0, 158.9, 151.1, 138.7, 131.6, 121.8, 91.6, 76.1, 71.3, 59.3, 47.3, 42.3, 36.3, 27.2, 19.4, −3.5, −3.7.

Preparation of Compound 16.

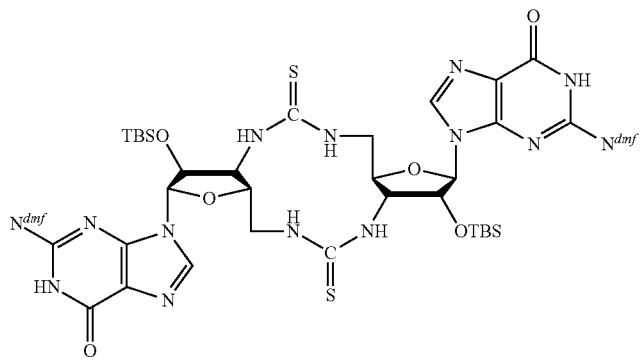

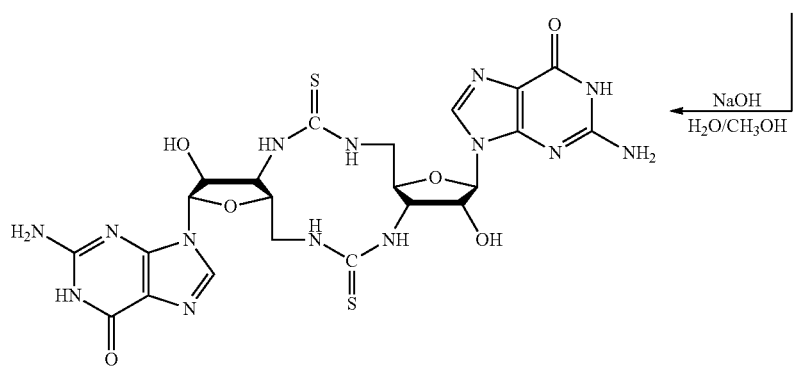

To 15 (230 mg, 0.23 mmol) dissolved in CH$_3$OH (5 mL) was added 4 N NaOH (5 mL). The solution was heated at 60° C. for 160 min, cooled in an ice bath, and neutralized with 1 N HCl (20 mL). The product came out of solution as a white solid on neutralization. The mixture was filtered and the residue washed with H$_2$O to give 16 (180 mg, 0.28 mmol, quant from 15), which was characterized as follows: m/z (M-H) 645.3 (calculated for C$_{22}$H$_{25}$N$_{14}$O$_6$S$_2{}^-$: 645.2); UV $\lambda_{max}$ 248 nm; $^1$H NMR (0.1 N NaOD in D$_2$O) 25° C.: δ 7.86 (s, 2H), 5.47 (d, J=8 Hz, 2H), 4.80 (ap t, J=8 Hz, 2H), 4.21 (ddd, J=11 Hz, 4 Hz, 2 Hz, 2H), 3.82 (dd, J=8 Hz, 2 Hz, 2H), 3.66 (dd, J=11 Hz, 4 Hz, 2H), 3.13 (ap t, J=11 Hz, 2H); $^{13}$C NMR (0.1 N NaOD in D$_2$O) 25° C.: δ 174.1, 168.4, 161.6, 152.6, 135.6, 117.9, 86.1, 83.4, 73.2, 57.2, 52.7.

Preparation of Compound 17.

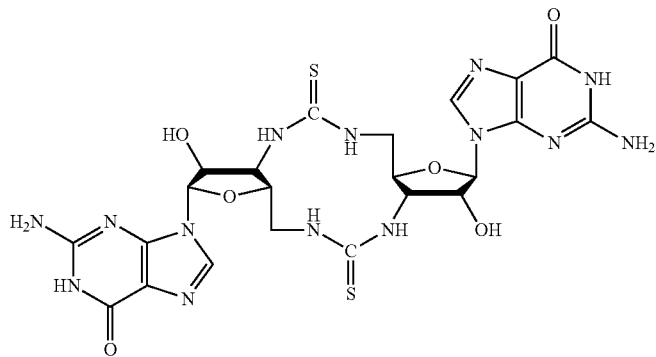

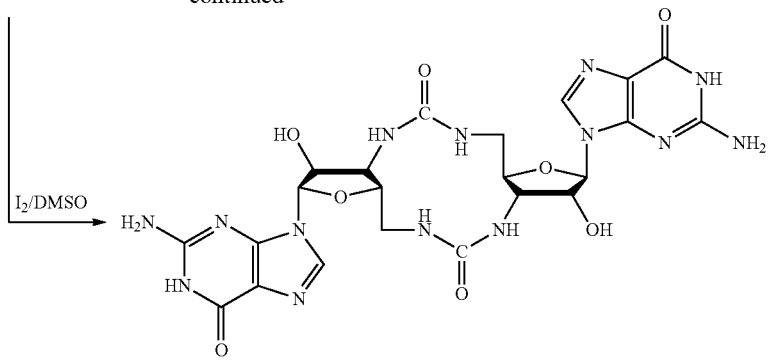

17

To 16 (65 mg, 100 µmol) dissolved in DMSO (1 mL) was added $I_2$ (12.5 mg, 50 µmol). The mixture was heated at 80° C. for 1 d, cooled and 1 mL $H_2O$ containing $Na_2S_2O_3$ (20 mg, 126 µmol) was added to precipitate the crude product. The precipitate was triturated with 0.1 N NaOH, filtered to remove sulfur, and the solution applied to the PRP column, then eluted using a gradient of 0.1 N NaOH to 50% $CH_3OH$ in 20 min. The product eluted at 70% of the gradient. The combined product fractions were concentrated to remove $CH_3OH$, and neutralized using $CO_2$. The product came out of solution as a white solid on neutralization. The mixture was filtered and the residue washed with $H_2O$ to give 17 (23 mg, 37 µmol, 37% from 16), which was characterized as follows: m/z (M-H) 613.3 (calculated for $C_{22}H_{25}N_{14}O_8^-$: 613.2); UV $\lambda_{max}$ 253 nm; $^1H$ NMR (0.5 N NaOD in $D_2O$) 65° C. because of aggregation: δ 7.67 (s, <2H because of exchange with solvent), 5.55 (d, J=1 Hz, 2H), 4.38-4.35 (m, 2H), 4.18-4.13 (m, 2H), 3.87-3.79 (m, 2H), 3.44-3.36 (m, 2H), 3.33-3.24 (m, 2H); $^{13}C$ NMR (0.5 N NaOD in $D_2O$) 65° C.: δ 167.1, 160.0, 158.6, 150.2, 122.9, 116.8, 90.0, 75.4, 67.3, 55.7, 40.9.

Preparation of Compounds 18 and 19a/b.

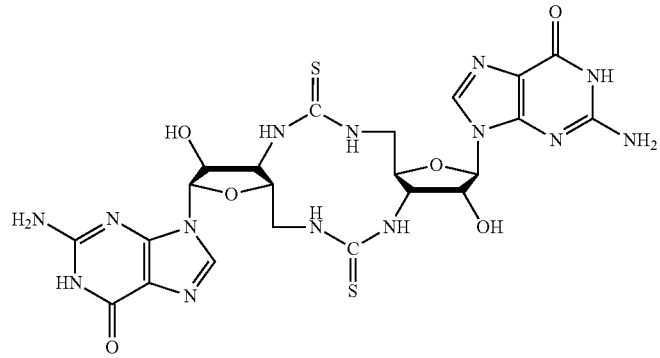

16

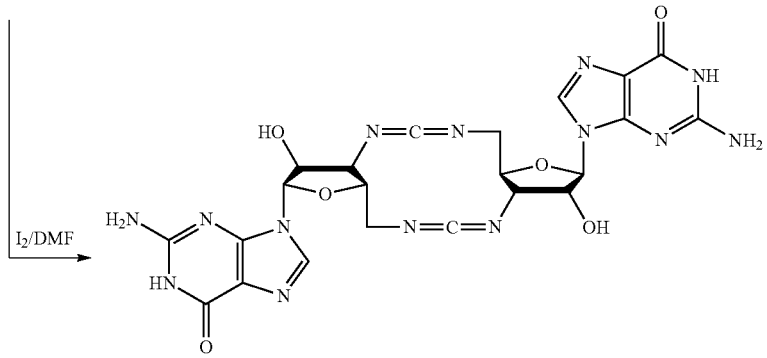

18

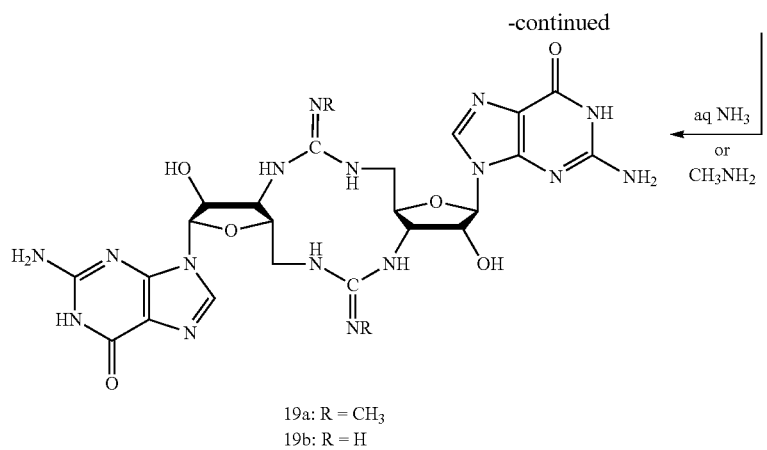

19a: R = CH₃
19b: R = H

To 16 (65 mg, 100 mol) suspended in DMF (2 mL) was added TEA (80 µL, 60 µmol) and I₂ (76 mg, 30 µmol). Heating at 60° C. for 30 min gave a clear, dark solution. The mixture was concentrated to remove DMF, triturated with 0.1 N NaOH, filtered to remove sulfur, and the solution applied to the PRP column, then eluted using a gradient of 0.1 N NaOH to CH₃OH in 50 min. The product eluted at 50% of the gradient. The combined product fractions were concentrated to remove CH₃OH, and neutralized using CO₂. The product came out of solution as a white solid on neutralization. The mixture was filtered and the residue washed with H₂O to give 18 (18 mg, 31 µmol, 31% from 16), which was characterized as follows: m/z (M-H) 577.3 (calculated for $C_{22}H_{21}N_{14}O_6$: 577.2); UV $\lambda_{max}$ 252 nm; $^1$H NMR (0.1 N NaOD in D₂O) 25° C.: δ 7.67 (s, 2H), 6.00 (d, J=1 Hz, 2H), 5.15 (dd, J=6 Hz, 1 Hz, 2H), 4.37 (dd, J=9 Hz, 6 Hz, 2H), 3.72 (dd, J=15 Hz, 3 Hz, 2H), 3.33-3.26 (m, 4H); $^{13}$C NMR (0.1 N NaOD in D₂O) 25° C.: δ 168.5, 163.0, 161.8, 151.2, 125.4, 117.7, 92.3, 87.1, 86.7, 67.3, 45.6.

To 16 (32 mg, 50 µmol) suspended in DMF (1 mL) was added TEA (30 µL, 20 µmol) and I₂ (26 mg, 100 µmol). After 1 h the mixture was partitioned between H₂O (1 mL) and CH₂Cl₂ (5 mL). The aqueous layer was concentrated to a solid and the solid dissolved in aq methylamine (40%, 1 mL). The mixture was heated at 60° C. for 2 d and concentrated. The residue was triturated with 0.1 N NaOH, filtered, applied to the PRP column, and eluted using a gradient of 0.1 N NaOH to CH₃OH in 40 min. The product eluted at 55% of the gradient. The combined product fractions were concentrated to remove CH₃OH, and neutralized using CO₂. The product came out of solution as a white solid on neutralization. The mixture was filtered and the residue washed with H₂O to give 19a (6 mg, 9 µmol, 19% from 16), which was characterized as follows: m/z (M-H) 639.3 (calculated for $C_{24}H_{31}N_{16}O_6^-$: 639.3); UV $\lambda_{max}$ 254 nm; $^1$H NMR (0.1 N NaOD in D₂O) 25° C.: δ 7.84 (s, 2H), 5.46 (d, 8 Hz, 2H), 4.84 (ap t, J=8 Hz, 2H), 4.27-4.19 (m, 2H), 3.73 (d, J=8 Hz, 2H), 3.23 (dd, J=10 Hz, 3 Hz, 2H), 2.97 (ap t, J=10 Hz, 2H), 2.72 (s, 6H); $^{13}$C NMR (0.1 N NaOD in D₂O) 25° C.: δ 168.5, 161.5, 155.9, 152.5, 135.6, 117.9, 86.4, 83.0, 73.5, 55.1, 46.8, 27.5.

To 16 (32 mg, 50 µmol) suspended in DMF (1 mL) was added TEA (30 µL, 20 µmol) and I₂ (26 mg, 100 µmol). After 95 min diethyl ether was added and the precipitate was isolated by filtration. To this precipitate was added conc aq NH₃ (1 mL), and after 1 d additional aq NH₃ was added (5 mL). The mixture was partitioned between H₂O (1 mL) and CH₂Cl₂ (5 mL), then heated at 60° for 2 weeks and concentrated. The residue was triturated with 0.1 N NaOH, filtered, applied to the PRP column, and eluted using a gradient of 0.1 N NaOH to CH₃OH in 40 min. The product eluted at 50% of the gradient. The combined product fractions were concentrated to remove CH₃OH, and neutralized using CO₂. The product came out of solution as a white solid on neutralization. The mixture was filtered and the residue washed with H₂O to give 19b (4 mg, 7 µmol, 13% from 16), which was characterized as follows: m/z (M-H) 611.3 (calculated for $C_{22}H_{27}N_{16}O_6^-$: 611.2); UV $\lambda_{max}$ 253 nm; $^1$H NMR (0.1 N NaOD in D₂O) 25° C.: δ 7.84 (s, 2H), 5.45 (d, J=8 Hz, 2H), 4.81 (ap t, J=8 Hz, 2H), 4.25 (d, J=10 Hz, 2H), 3.74 (d, J=7 Hz, 2H), 3.30-3.19 (m, 2H), 3.02 (ap t, J=11 Hz, 2H); $^{13}$C NMR (0.1 N NaOD in D₂O) 25° C.: δ 168.4, 161.5, 156.1, 152.6, 135.4, 117.8, 86.0, 83.1, 73.3, 55.3, 47.1.

Example 2

The following illustrate representative pharmaceutical dosage forms, containing a compound of formula I ('Compound X'), for therapeutic or prophylactic use in humans.

| (i) Tablet 1 | mg/tablet |
|---|---|
| Compound X = | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| Compound X = | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| Compound X = | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/ml) | mg/ml |
|---|---|
| Compound X = (free acid form) | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/ml) | mg/ml |
|---|---|
| Compound X = (free acid form) | 10.0 |
| Monobasic sodium phosphate | 0.3 |
| Dibasic sodium phosphate | 1.1 |
| Polyethylene glycol 400 | 200.0 |
| 1.0N Sodium hydroxide solution (pH adjustment to 7.0-7.5) | q.s. |
| Water for injection | q.s. ad 1 mL |

| (vi) Aerosol | mg/can |
|---|---|
| Compound X = | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A compound of formula I:

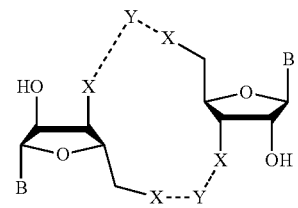

wherein:
when the dashed bonds are single bonds, then each X is $NR^a$, and each Y is independently $C(=O)$, $C(=S)$ or $C(=NR^b)$; or when the dashed bonds are double bonds, then each X is N, and each Y is C;
each $R^a$ is independently H or $(C_1\text{-}C_6)$alkyl;
each $R^b$ is independently H or $(C_1\text{-}C_6)$alkyl; and
each B is independently

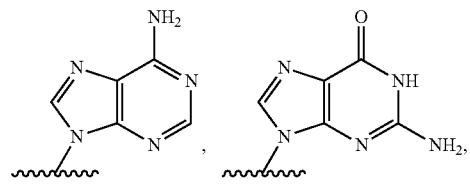

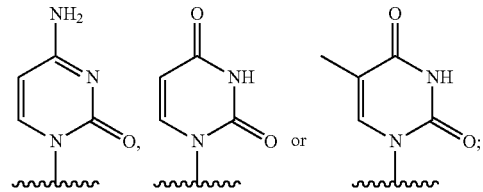

or a pharmaceutically acceptable salt thereof.

2. The compound of claim 1, wherein the dashed bonds are single bonds, each X is $NR^a$, and each Y is independently $C(=O)$, $C(=S)$ or $C(=NR^b)$.

3. The compound of claim 1, wherein each $R^a$ is H.

4. The compound of claim 1, wherein each Y is $C(=O)$.

5. The compound of claim 1, wherein each Y is C(=S).

6. The compound of claim 1, wherein each Y is C(=NR$^b$).

7. The compound of claim 1, wherein each R$^b$ is independently H or methyl.

8. The compound of claim 1, wherein each R$^b$ is H.

9. The compound of claim 1, wherein each R$^b$ is methyl.

10. The compound of claim 1, wherein the dashed bonds are double bonds, each X is N, and each Y is C.

11. The compound of claim 1, wherein each B is:

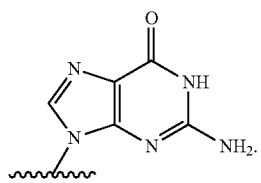 [SMILES: *n1cnc2c(=O)[nH]c(N)nc21]

12. The compound of claim 1 which is selected from:

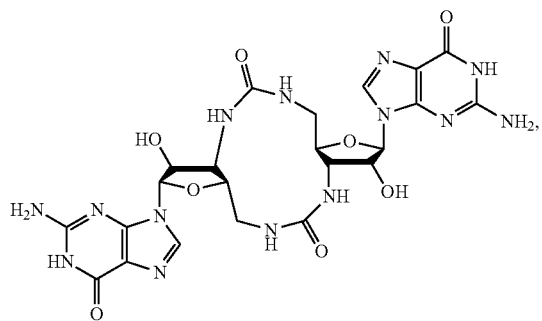

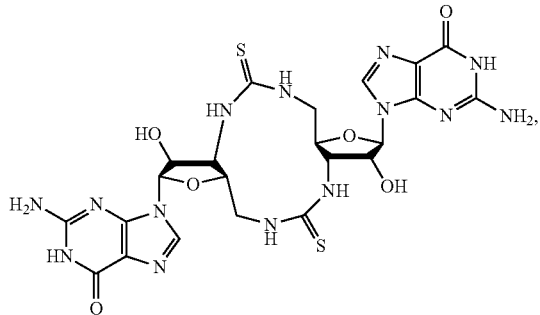

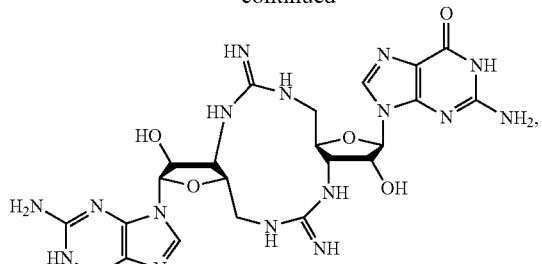

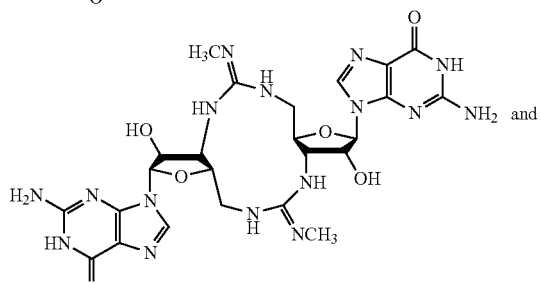

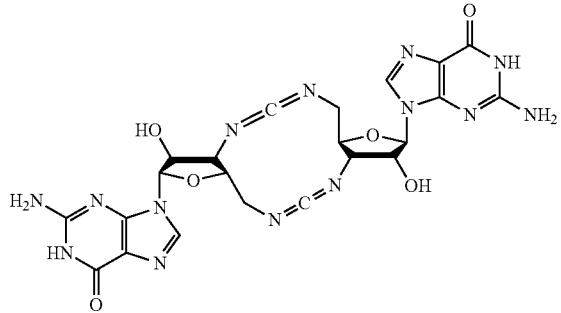

and pharmaceutically acceptable salts thereof.

13. A pharmaceutical composition comprising a compound of formula I as described in claim 1, or a pharmaceutically acceptable salt thereof and a pharmaceutically acceptable carrier.

14. A method to treat a bacterial infection in a mammal in need thereof, comprising administering an effective amount of a compound of formula I as described in claim 1 or a pharmaceutically acceptable salt thereof to the mammal.

* * * * *

UNITED STATES PATENT AND TRADEMARK OFFICE
CERTIFICATE OF CORRECTION

PATENT NO. : 9,315,523 B2
APPLICATION NO. : 14/562203
DATED : April 19, 2016
INVENTOR(S) : Roger A. Jones and Barbara L. Gaffney It is certified that error appears in the above-identified patent and that said Letters Patent is hereby corrected as shown below:

In the Specification

Column 1, Lines 12-14, please delete "This invention was made with government support under GM79760 awarded by the National Institutes of Health. The government has certain rights in the invention." and insert -- This invention was made with government support under grant number GM079760 awarded by the National Institutes of Health. The government has certain rights in the invention. -- therefor.

Signed and Sealed this
Third Day of January, 2023

Katherine Kelly Vidal
*Director of the United States Patent and Trademark Office*